US006627744B2

(12) United States Patent
Davis et al.

(10) Patent No.: US 6,627,744 B2
(45) Date of Patent: Sep. 30, 2003

(54) SYNTHESIS OF GLYCODENDRIMER REAGENTS

(75) Inventors: Benjamin G. Davis, Durham (GB); John Bryan Jones, Lakefield (CA); Richard R. Bott, Burlingame, CA (US)

(73) Assignee: Genencor International, Inc., Palo Alto, CA (US)

( * ) Notice: Subject to any disclaimer, the term of this patent is extended or adjusted under 35 U.S.C. 154(b) by 310 days.

(21) Appl. No.: 09/824,827

(22) Filed: Apr. 2, 2001

(65) Prior Publication Data

US 2002/0019039 A1 Feb. 14, 2002

(51) Int. Cl.$^7$ ............................ C07H 17/00; C07H 1/00

(52) U.S. Cl. .................... 536/18.6; 536/4.1; 536/18.5; 536/118; 536/122; 536/123.1; 536/124; 536/17.9

(58) Field of Search ................................ 536/4.1, 18.5, 536/18.6, 118, 122, 123.1, 124, 17.9

(56) References Cited

U.S. PATENT DOCUMENTS

| | | | |
|---|---|---|---|
| 5,208,158 A | 5/1993 | Bech et al. | 435/219 |
| 5,244,791 A | 9/1993 | Estell | 435/68.1 |
| 5,316,935 A | 5/1994 | Arnold et al. | 435/222 |
| 5,316,941 A | 5/1994 | Estell et al. | 435/252.3 |
| 5,340,735 A | 8/1994 | Christianson et al. | 435/221 |
| 5,403,737 A | 4/1995 | Abrahmsen et al. | 435/252.3 |
| 5,629,173 A | 5/1997 | Abrahmsen et al. | 435/68.1 |
| 5,955,340 A | 9/1999 | Bott et al. | 435/221 |
| 6,310,043 B1 * | 10/2001 | Bundle et al. | 514/25 |
| 6,417,339 B1 * | 7/2002 | Wiessler et al. | 536/4.1 |

FOREIGN PATENT DOCUMENTS

| | | |
|---|---|---|
| EP | 3 328 229 A1 | 8/1989 |
| WO | WO 91/16423 | 4/1991 |
| WO | WO 96/27671 | 2/1996 |
| WO | WO 97/37007 | 10/1997 |
| WO | WO 98/23732 | 6/1998 |
| WO | WO 99/20723 | 4/1999 |
| WO | WO 99/37323 | 7/1999 |
| WO | WO 99/37324 | 7/1999 |
| WO | WO 00/01712 | 1/2000 |

OTHER PUBLICATIONS

Bech et al., "Significance of Hydrophobic $S_4$–$P_4$ Interactions in Subtilisin 309 from *Bacillus ientus*," *Biochemistry*, 32:2847–2852 (1993).

Bech, L.M., et al., "Chemical Modifications of a Cysteinyl Residue Introduced in the Binding Site of Carboxypeptidase Y by Site–Directed Mutagenesis," *Carsberg Research Communications*, (1988) vol. 53, pp. 381–393, XP002063095.

Bergland, P., et al., "Chemical Modification of Cystein Mutants of Subtilisin Bacillus Lentus Can Create Better Catalysts Than the Wild–Type Enzyme," *J. Am. Chem. Soc.*, 119:5265–5266 (1997).

Berglund et al., "Altering the Specificity of Subtilisin *B. lentus* by Combining Site–Directed Mutagenesis and Chemical Modification," *Bioorganic & Mechanical Chemistry Letters*, 6:2507–2512 (1996).

Betzel et al., "Crystal Structure of the Alkaline Proteinase Savinase# from *Bacillus lentus* at 1 4 Å Resolution," *J. Mol. Biol.*, 223:427–445(1992).

Bonneau et al., "Alteration of the Specificity of Subtilisin BPN' by Site–Directed Mutagenesis in its $S_1$ and $S_1'$ Binding Sites," *J. Am. Chem. Soc.*, 113:1026–30 (1991).

Brocklehurst, "Specific Covalent Modification of Thiols: Applications in the Study of Enzymes and Other Biomolecules," *Int. J. Biochem.*, 10:259–274 (1979).

Bruice et al., "Novel Alkyl Alkanethiolsulfonate Sulfhydryl Reagents. Modification of Derivatives of L–Cysteine," *Journal of Protein Chemistry*, 1:47–58 (1982).

Chen et al., "Probing the S–1' Subsite Selectivity of an Industrial Alkaline Protease in Anhydrous t–Butanol," *Bioorganic & Medicinal Chemistry Letters*, 3(4):727–33 (1993).

Davies et al., "A Semisynthetic Metalloenzyme Based on a Protein Cavity That Catalyzes the Enantiosleective Hydrolysis of Ester and Amide Substrates," *J. Am. Chem. Soc.*, 119:11643–11652 (1997).

Davis, B.G., et al., "Altering the specificity of subtilisin *Bacillus lentus* through the introduction of positive charge at single amino acid sites," *Bioorganic and Medicinal Chemistry*, (Nov. 1999) 7 (11) 2303–11, XP0000892841.

(List continued on next page.)

*Primary Examiner*—Kathleen K. Fonda
(74) *Attorney, Agent, or Firm*—H. Thomas Anderton, Jr.

(57) ABSTRACT

The present invention relates to a chemically modified mutant protein including a cysteine residue substituted for a residue other than cysteine n a precursor protein, the substituted cysteine residue being subsequently modified by reacting the cysteine residue with a glycosylated thiosulfonate. Also a method of producing the chemically modified mutant protein is provided. The present invention also relates to a glycosylated methanethiosulfonate. Another aspect of the present invention is a method of modifying the functional characteristics of a protein including providing a protein and reacting the protein with a glycosylated methanethiosulfonate reagent under conditions effective to produce a glycoprotein with altered functional characteristics as compared to the protein. In addition, the present invention relates to methods of determining the structure-function relationships of chemically modified mutant proteins. The present invention also relates to synthetic methods for producing thio-glycoses, the thio-glycoses so produced, and to methods for producing glycodendrimer reagents.

38 Claims, 20 Drawing Sheets

OTHER PUBLICATIONS

Davis, B.G., et al., "Controlled site selective glycosylation of proteins by a combined site directed mutagenesis and chemical modification approach," *J. Org., Chem.*, vol. 63, (1998), pp. 9614–9615, XP002135378.

Davis, B.G., et al., "Controlled site selective protein glycosilation for precise glycan structure catalytic activity relationships," *Bioorganic & Medicinal Chemistry*, 8, 1527–1535, (2000), XP000986502.

Davis, B. G., et al., "Glycomethanethiosulfonates: powerful reagents for protein glycosylation," *Tetrahedron: Asymmetry, NL, Elsevier Science Publishers*, Amsterdam, 11:1, 245–262 (2000–01), XP004191784.

Davis, B.G., et al., "The controlled introduction of multiple negative charge at single amino acid sites in subtilisin bacillus lentus," *Bioorganic and Medicinal Chemistry*, (Nov. 1999) 7 (11) 2293–301, XP0000892840.

DeSantis et al., "Chemical Modifications as a Single Site Can Induce Significant Shifts in the pH Profiles of a Serine Protease," *J. Am. Chem. Soc.*, 120:8582–8586 (1998).

DeSantis et al., "Site–Directed Mutagenesis Combined with Chemical Modification as a Strategy for Altering the Specificity of the S1 and S1' Pockets of Subtilisin *Bacillus ientus*," *Biochemistry*, 37:5968–5973 (1998), XP002135377.

Desantis, G., et al, "Probing the altered specificity and catalytic properties of mutant subtilisin chemically modified at position S156C and S166C in the S1 pocket," *Bioorganic and Medicinal Chemistry*, (1997) 7/7 (1381–1387), XP0000892843.

Dickman, M., et al., "Chemically modified mutants of subtilisin bacillus lentus catalyze transesterification reactions better than wild type," *Tetrahedron Asymmetry*, (Dec. 11, 1998) 9/23 4099–4102.

Gron et al., "A Highly Active and Oxidation–Resistant Subtilisin–Like Enzyme Produced by a Combination of Site–Directed Mutagenesis and Chemical Modification," *Eur. J. Biochem.*, 194:897–901 (1990).

International Search Report, mailed Jul. 21, 2000 from corresponding PCT US99/30362.

International Search Report, mailed Mar. 20, 2000, from corresponding PCT US99/15138.

International Search Report, mailed Jul. 10, 2001, from corresponding PCT US00/10988.

Kaiser, "Catalytic Activity of Enzymes Altered at Their Active Sites," *Agnew. Chem. Int. Ed. Engl.*, 27–913–922 (1988).

Kawase et al., "Effect of Chemical Modification of Tyrosine Residues on Activities of Bacterial Lipase," *Journal of Fermentation and Bioengineering*, 72:317–319 (1991).

Kenyon et al., "Novel Sulfhydryl Reagents," *Methods Enzymol.*, 47:407–430 (1977).

Kluger et al., "Amino Group Reactions of the Sulfhydryl Reagent Methyl Methanesulfonothioate. Inactivation of D–3–hydroxybutyrate Dehydrogenase and Reaction with Amines in Water," *Can. J. Biochem.*, 58:629–632 (1980).

Lloyd, R.C, et al., "Site selective glycosilation of subtilisin bacillus lentus causes dramatic increase in esterase activity," *Biorganic & Medicinal Chemistry*, 8, 1537–1544 (2000), XP000986506.

Lo, Bryan, et al., "Replacement of Ala–166 with Cysteine in the HighAffinity Rabbit SodiumBlucose Transporter Alters Transpoert Kinetics and Allows Methanethiosulfonate Ethylamine to Inhibit Transporter Function," *The Journal of Biological Chemistry*, 273:2 903–909 (1998).

Neet, K.E. and Koshland, D.E., "The Conversion of Serine at the Active Site of Subtilisin to Cysteine: A 'Chemical Mutation,'" *Proc. Nat. Acad. Sci. USA*, 56(5):1606–1611. (1966).

Nishimura et al., "Reversible Modification of the Sulfhydryl Groups of *Escherichia coli* Succinic Thiokinase with Methanethiolating Reagents, 5,5'–Dithio–bis(2–Nitrobenzoic Acid), p–Hydroxymercuribenzoate, and Ethylmercurithiosalicylate," *Archives of Biochemistry and Biophysics*, 170:461–467 (1975).

Paulson, J.C., "Glycoproteins: what are the sugar chains for?" *TIBS*, 14:272–276 (1989).

Planas et al., "Reengineering the Catalytic Lysine of Aspartate Aminotransferase by Chemical Elaboration of a Genetically Introduced Cysteine," *Biochemistry*, 30:8268–8276 (1991).

Plettner et al., "A Combinatorial Approach to Chemical Modification of Subtilisin *Bacillus ientus*," *Bioorganic & Medicinal Chemistry Letters*, 8:2291–2296 (1998), XP004138220.

Plettner, E., et al., "Modulation of Esterase and Amidase Activity of Subtilisin Bacillus Lentus by Chemical Modification of Cysteine Mutants," *Journal of the American Chemical Society*, (Jun. 2, 1999) 121/21, 4977–4981, XPO000891274.

Polgar et al., "A New Enzyme Containing a Synthetically Formed Active Site. Thiol–Subtilisin," *Journal of American Chemical Society*, 88:3153–3154 (1966).

Ramachandran et al., "Stabilization of Barstar by Chemical Modification of the Buried Cysteines," *Biochemistry*, 35:8776–8785 (1996).

Roberts et al., "Reactivity of Small Thiolate Anions and Cystein–25 in Papain Toward Methyl Methanethiosulfonate," *Biochemistry*, 25:5595–5601 (1986).

Siddiqui et al, "Arthrobacter D–Xylose Isomerase: Chemical Modification of Carboxy Groups and Protein Engineering Of pH Optimum," *Biochem. J.*, 295:685–691 (1993).

Smith et al., "An Engineered Change in Substrate Specificity of Ribulosebisphosphate Carboxylase/Oxygenase," *The Journal of Biological Chemistry*, 265:1243–1245 (1990).

Smith et al., "Chemical Modification of Active Site Residues in γ–Glutamyl Transpeptidase," *The Journal of Biological Chemistry*, 270:12476–12480 (1995).

Smith et al., "Simple Alkanethiol Groups for Temporary Blocking of Sulfhydryl Groups of Enzymes," *Biochemistry*, 14:766–771 (1975).

Smith et al., "Subtle Alteration of the Active Site of Ribulose Bisphosphate Carboxylase/Oxygenase by Concerted Site–Directed Mutagenesis and Chemical Modification," *Biochemical and Biophysical Research Communications*, 152:579–584 (1988).

Spura, Armin, et al., "Probing the Agonist Domain of the Nicotinic Acetylcholine Receptor by Cysteine Scanning Mutagenesis Reveals Residues in Proximity to the α–Bungarotoxin Binding Site," *Biochemistry*, 38:4912–4921 (1999).

Stewart et al., "Catalytic Oxidation of Dithiols by a Semi-synthetic Enzyme," *J. Am. Chem. Soc.*, 108:3480–3483 (1986).

Valenzuela et al., "Kinetic Properties of Succinylated and Ethylenediamine–Amidated δ–Chymotrypsins," *Biochim. Biophys. Acta*, 250:538–548 (1971).

West et al., "Enzymes as Synthetic Catalysts: Mechanistic and Active–Site Considerations of Natural and Modified Chymotrypsin," *J. Am. Chem. Soc.*, 112:5313–5320 (1990).

White et al., "Sequential Site–Directed Mutagenesis and Chemical Modification to Convert the Active Site Arginine 292 Of Aspartate Aminotransferase to Homoarginine," *Journal of the American Chemical Society*, 114:292–293 (1992).

Wynn et al., "Chemical Modification of Protein Thiols: Formation of Mixed Disulfides," *Methods in Enzymology*, 251:351–356 (1995).

Wynn et al., "Comparison of Straight Chain and Cyclic Unnatural Amino Acids Embedded in the Core of Staphylococcal Nuclease," *Protein Science*, 6:1621–1626 (1997).

Wynn et al., "Mobile Unnatural Amino Acid Side Chains in the Core of Staphylococcal Nuclease," *Protein Science*, 5:1026–1031 (1996).

Wynn et al., "Unnatural Amino Acid Packing Mutants of *Escherichia coli* Thioredoxin Produced by Combined Mutagenesis/Chemical Modification Techniques," *Protein Science*, 2:395–403 (1993).

Davis, B.G., et al., "The controlled glycosylation of a protein with a bivalent glycan: towards a new class of glycoconjugates, glycodendriproteins," Chem. Commun, 2001, pp. 351–352.

Davis, B.G., et al., "Glycosyldisulfides: a new class of solution and solid phase glycosyl donors," Chem. Commun, 2001, pp. 189–190.

* cited by examiner

Type A TREN-type

First Generation

Second Generation

Type B Penta-E type

First Generation

Second Generation where
X = nothing or S or S(CH$_2$)$_2$O or S(CH$_2$)$_3$O or S(CH$_2$)$_4$O; Y = O or SS or (CH$_2$)$_2$O or S(CH$_2$)$_3$O or S(CH$_2$)$_4$O;
A = SS or O; [P] = H or Ac or Bn

Type C - ArGal type

First Generation

Second Generation

Type AC₂ Hybrid

Second Generation

Type CA₂ Hybrid

Second Generation where
X = nothing or S or S(CH₂)₂O or S(CH₂)₃O or S(CH₂)₄O; Y = O or SS or (CH₂)₂O or S(CH₂)₃O or S(CH₂)₄O;
A = SS or O; [P] = H or Ac or Bn, Z = H or CH₃

Lectin  Glyco  dendri  protein

Glycodendriprotein

Normal Addition

Inverse Addition

Scheme 1

Scheme 2

Scheme 3

Scheme 4

Scheme 5

5β

Scheme 6

Glycodendrimer proteins from 7'a, 7'b

Scheme 8

Scheme 9

Scheme 10

Scheme 11

Scheme 12

Scheme 13

Scheme 14

Scheme 15

Scheme 16

Scheme 17

| | | 42 | |
|---|---|---|---|
| Normal addition | 4% | 5% | 91% |
| DMF, slow addition, high dilution | 6% | 9% | 56% |
| cat Bu₄NI, toluene | 21% | 17% | 47% |

Scheme 18

Scheme 19

Scheme 20

Scheme 21

S156C-SS-ArGal-(SS-Gal)$_2$

SYNTHESIS OF GLYCODENDRIMER REAGENTS

RELATED APPLICATION DATA

This application claims the benefit of U.S. patent application Ser. No. 09/347,029, filed Jul. 2, 1999, now U.S. Pat. No. 6,512,098, and Ser. No. 09/556,466, filed Apr. 21, 2000 and which are hereby incorporated by reference.

FIELD OF THE INVENTION

The present invention relates to chemically modified mutant proteins having modified glycosylation patterns with respect to a precursor protein from which they are derived. In particular, the present invention relates to a chemically modified mutant protein including a cysteine residue substituted for a residue other than cysteine in a precursor protein, the substituted cysteine residue being subsequently modified by reacting the cysteine residue with a glycosylated thiosulfonate. The present invention also relates to a method of producing the chemically modified mutant proteins and glycosylated methanethiosulfonate reagents. Another aspect of the present invention is a method of modifying the functional characteristics of a protein by reacting the protein with a glycosylated methanethiosulfonate reagent. The present invention also relates to methods of determining the structure-function relationships of chemically modified mutant proteins.

BACKGROUND OF THE INVENTION

Modifying enzyme properties by site-directed mutagenesis has been limited to natural amino acid replacements, although molecular biological strategies for overcoming this restriction have recently been derived (Cornish et al., *Angew. Chem.*, Int. Ed. Engl., 34:621–633 (1995)). However, the latter procedures are difficult to apply in most laboratories. In contrast, controlled chemical modification of enzymes offers broad potential for facile and flexible modification of enzyme structure, thereby opening up extensive possibilities for controlled tailoring of enzyme specificity.

Changing enzyme properties by chemical modification has been explored previously, with the first report being in 1966 by the groups of Bender (Polgar, et al., *J. Am. Chem. Soc.*, 88:3153–3154 (1966)) and Koshland meet et al., *Proc. Natl. Acad. Sci. USA*, 56:1606–1611 (1966)), who created a thiolsubtilisin by chemical transformation ($CH_2OH \rightarrow CH_2SH$) of the active site serine residue of subtilisin BPN' to cysteine. Interest in chemically produced artificial enzymes, including some with synthetic potential, was reviewed by Wu (Wu et al., *J. Am. Chem. Soc.*, 111:4514–4515 (1989); Bell et al., *Biochemistry*, 32:3754–3762 (1993)) and Peterson (Peterson et al., *Biochemistry*, 34:6616–6620 (1995)), and more recently, Suckling (Suckling et al., *Bioorg. Med. Chem. Lett.*, 3:531–534 (1993)).

Enzymes are now widely accepted as useful catalysts in organic synthesis. However, natural, wild-type, enzymes can never hope to accept all structures of synthetic chemical interest, nor always be transformed stereospecifically into the desired enantiomerically pure materials needed for synthesis. This potential limitation on the synthetic applicabilities of enzymes has been recognized, and some progress has been made in altering their specificities in a controlled manner using the site-directed and random mutagenesis techniques of protein engineering. However, modifying enzyme properties by protein engineering is limited to making natural amino acid replacements, and molecular biological methods devised to overcome this restriction are not readily amenable to routine application or large scale synthesis. The generation of new specificities or activities obtained by chemical modification of enzymes has intrigued chemists for many years and continues to do so.

U.S. Pat. No. 5,208,158 to Bech et al. ("Bech") describes chemically modified detergent enzymes where one or more methionines have been mutated into cysteines. The cysteines are subsequently modified to confer upon the enzyme improved stability towards oxidative agents. The claimed chemical modification is the replacement of the thiol hydrogen with $C_1$-6 alkyl.

Although Bech has described altering the oxidative stability of an enzyme though mutagenesis and chemical modification, it would also be desirable to develop one or more enzymes with altered properties such as activity, nucleophile specificity, substrate specificity, stereoselectivity, thermal stability, pH activity profile, and surface binding properties for use in, for example, detergents or organic synthesis. In particular, enzymes, such as subtilisins, tailored for peptide synthesis would be desirable. Enzymes useful for peptide synthesis have high esterase and low amidase activities. Generally, subtilisins do not meet these requirements and the improvement of the esterase to amidase selectivities of subtilisins would be desirable. However, previous attempts to tailor enzymes for peptide synthesis by lowering amidase activity have generally resulted in dramatic decreases in both esterase and amidase activities. Previous strategies for lowering the amidase activity include the use of water-miscible organic solvents (Barbas et al., *J. Am. Chem. Soc.*, 110:5162–5166(1988); Wong et al., *J. Am. Chem. Soc.*, 112:945–953 (1990); and Sears et al., *Biotechnol. Proc.*, 12:423–433 (1996)) and site-directed mutagenesis (Abrahamsen et al., *Biochemistry.* 303:4151–4159 (1991); Bonneau et al., "Alteration of the Specificity of Subtilisin BPN' by Site-Directed Mutagenesis in its S1 and S1' Binding-Sites," *J. Am. Chem. Soc.*, 113:1026–1030(1991); and Graycar et al., *Annal. N.Y. Acad. Sci.*, 67:71–79 (1992)). However, while the ratios of esterase-to-amidase activities were improved by these approaches, the absolute esterase activities were lowered concomitantly. Abrahamsen, et al. *Biochemistry* 30:4151–4159 (1991). Chemical modification techniques (Neet et al., *Proc. Nat. Acad. Sci. USA*, 54:1606 (1966); Polgar et al., *J. Am. Chem. Soc.*, 88:3153–3154(1966); Wu et al., *J. Am. Chem. Soc.*, 111:4514–4515 (1980); and West et al., *J. Am. Chem. Soc.*, 112:5313–5320(1990), which permit the incorporation of unnatural amino acid moieties, have also been applied to improve the esterase to amidase selectivity of subtilisins. For example, chemical conversion of the catalytic triad serine (221) of subtilisin to cysteine (Neet et al., *Proc. Natl. Acad. Sci.*, 54:1606 (1966); Polgar et al., *J. Am. Chem. Soc.* 88:3153–3154 (1966); and Nakatsuka et al., *J. Am. Chem. Soc.*, 109:3808–3810 (1987)) or to selenocysteine (Wu et al., *J. Am. Chem. Soc.*, 111:4514–4515 (1989)), and methylation of the catalytic triad histidine (His57) of chymotrypsin (West et al., *J. Am. Chem. Soc.*, 112:5313–5320 (1990)), effected substantial improvement in esterase-to-amidase selectivities. Unfortunately however, these modifications were again accompanied by 50- to 1000-fold decreases in absolute esterase activity.

Surface glycoproteins act as markers in cell—cell communication events that determine microbial virulence (Sharon et al., *Essays Biochem.*, 30:59–75 (1995)), inflammation (Lasky, *Annu. Rev. Biochem.*, 64:113–139 (1995);

Weis et al., *Annu. Rev. Biochem.*, 65:441–473 (1996)), and host immune responses (Varki, *Glycobiol.*, 3:97–130 (1993); Dwek, *Chem. Rev.*, 96:683–720 (1996)). In addition, the correct glycosylation of proteins is critical to their expression and folding (Helenius, *Mol. Biol. Cell*, 5:253–265 (1994)) and increases their thermal and proteolytic stability (Opendakker et al., *FASEB J.*, 7:1330–1337 (1993)). Glycoproteins occur naturally in a number of forms (glycoforms) (Rademacher et al., *Annu. Rev. Biochem.*, 57:785–838 (1988)) that possess the same peptide backbone, but differ in both the nature and site of glycosylation. The differences exhibited (Rademacher et al., *Annu. Rev. Biochem.*, 57:785–838 (1988); Parekh et al., *Biochem.*, 28:7670 7679 (1989); Knight, *Biotechnol.*, 7:35–40 (1989)) by each component within these microheterogeneous mixtures present regulatory difficulties (Liu, *Trends Biotechnol.*, 10:114–120 (1992); Bill et al., *Chem. Biol.*, 3:145–149 (1996)) and problems in determining exact function. To explore these key properties, there is a pressing need for methods that will not only allow the preparation of pure glycosylated proteins, but will also allow the preparation of non-natural variants for the determination of structure-function relationships, such as structure-activity relationships (SARs). The few studies that have compared single glycoforms successfully have required abundant sources and extensive chromatographic separation (Rudd et al., *Biochem.*, 33:17–22 (1994)).

Neoglycoproteins (Krantz et al, *Biochem.*, 15:3963–3968 (1976)), formed via unnatural linkages between sugars and proteins, provide an invaluable alternative source of carbohydrate-protein conjugates (For reviews see Stowell et al., *Adv. Carbohydr. Chem. Biochem.*, 37:225–281 (1980); *Neoglycoconiugates: Preparation and Applications*, Lee et al., Eds., Academic Press, London (1994); Abelson et al., *Methods Enzymol.*, 242: (1994); Lee et al., *Methods Enzymol.*, 247: (1994); Bovin et al., *Chem. Soc. Rev.*, 24:413–421 (1995)). In particular, chemical glycosylation allows control of the glycan structure and the nature of the sugar-protein bond. However, despite these advantages, existing methods for their preparation (Stowell et al., *Adv. Carbohvdr. Chem. Biochem.*, 37:225–281 (1980)) typically generate mixtures. In addition, these techniques may alter the overall charge of the protein (Lemieux et al., *J. Am. Chem. Soc.*, 97:4076–4083 (1975); Kobayashi et al., *Methods Enzymol.*, 247:409–418 (1994)) or destroy the cyclic nature of glycans introduced (Gray, *Arch. Biochem. Biophys.*, 163:426–428 (1974)). For example, the reductive amination of lactose with bovine serum albumin (BSA) caused indiscriminate modification of lysine residues through the formation of acyclic amines introduced (Gray, *Arch. Biochem. Biophys.*, 163:426–428 (1974)). Advances in the site-specific glycosylation of BSA have been made (Davis et al., *Tetrahedron Lett.*, 32:67936796 (1991); Wong et al., *Biochem. J.*, 300:843–850 (1994); Macindoe et al.,*J. Chem. Soc. Chem. Commun.* 847–848 (1998)). However, these techniques rely upon modification of an existing cysteine in BSA and, as such, allow no flexibility in the choice of glycosylation site. Glycoproteins occur naturally as complex mixtures of differently glycosylated forms which are difficult to separate. To explore their properties, there is a need for homogenous sources of carbohydrate-protein conjugates. Existing methods typically generate product protein mixtures of poorly characterized composition, with little or no control over the site or level of glycosylation.

The present invention is directed to overcoming these deficiencies.

SUMMARY OF THE INVENTION

It is an object of the present invention to provide for novel glycosylated proteins.

It is a further object of the invention to provide for novel glycoslyated proteins that have improved functional characteristics.

It is a further object of the invention to provide a method of producing glycosylated proteins which have well defined properties, for example, by having predetermined glycosylation patterns.

According to the present invention, a method is provided wherein the glycosylation pattern of a protein is modified in a predictable and repeatable manner. Generally, the modification of the protein occurs via reaction of a cysteine residue in the protein with a glycosylated thiosulfonate.

Thus, in one composition aspect of the invention, a chemically modified mutant ("CMM") protein is provided, wherein said mutant protein differs from a precursor protein by virtue of having a cysteine residue substituted for a residue other than cysteine in said precursor protein, the substituted cysteine residue being subsequently modified by reacting said cysteine residue with a glycosylated thiosulfonate. Preferably, the glycosylated thiosulfonate is an alkylthiosulfonate, most preferably a methanethiosulfonate.

In a method aspect of the present invention, a method of producing a chemically modified mutant protein is provided comprising the steps of: (a) providing a precursor protein; (b) substituting an amino acid residue other than cysteine in said precursor protein with a cysteine; (c) reacting said substituted cysteine with a glycosylated thiosulfonate, said glycosylated thiosulfonate comprising a carbohydrate moiety; and (d) obtaining a modified glycosylated protein wherein said substituted cysteine comprises a carbohydrate moiety attached thereto. Preferably, the glycosylated thiosulfonate is an alkylthiosulfonate, most preferably, a methanethiosulfonate. Also preferably, the substitution in said precursor protein is obtained by using recombinant DNA techniques by modifying a DNA encoding said precursor protein to comprise DNA encoding a cysteine at a desired location within the protein.

The present invention also relates to novel glycosylated thiosulfonates. In a preferred embodiment, the glycosylated thiosulfonate is a methanethiosulfonate. In a most preferred embodiment, the glycosylated methanethiosulfonate comprises a chemical structure including:

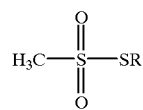

where R comprises -β-Glc, -Et-β-Gal, -Et-β-Glc, -Et-α-Glc,-Et-α-Man, -Et-Lac, -β-Glc(Ac)$_2$, -B-Glc(Ac)$_3$, -β-Glc(Ac)$_4$, -Et-α-Glc(Ac)$_2$, -Et-α-Glc(Ac)$_3$, -Et-α-Glc(Ac)$_4$, -Et-β-Glc(Ac)$_2$, -Et-β-Gal(Ac)$_4$, -Et-Lac(Ac)$_5$, -Et-Lac(Ac)$_6$, or Et-Lac(Ac)$_7$.

Another aspect of the present invention is a method of modifying the functional characteristics of a protein including reacting the protein with a glycosylated thiosulfonate reagent under conditions effective to produce a glycoprotein with altered functional characteristics as compared to the protein. Accordingly, the present invention provides for modified protein, wherein the protein comprises a wholly or partially predetermined glycosylation pattern which differs from the glycosylation pattern of the protein in its precursor, natural, or wild type state and a method for producing such a modified protein.

The present invention also relates to methods of determining the structure-function relationships of chemically modified mutant proteins. One method includes providing first and second chemically modified mutant proteins of the present invention, wherein the glycosylation pattern of the second chemically modified mutant protein differs from the glycosylation pattern of the first chemically modified mutant protein, evaluating a functional characteristic of the first and second chemically modified mutant proteins and correlating the functional characteristic of the first and second chemically modified mutant proteins with the structures of the first and second chemically modified mutant proteins. Another method involves providing first and second chemically modified mutant proteins of the present invention, wherein at least one different cysteine residue in the second chemically modified mutant protein is modified by reacting said cysteine residue with a glycosylated thiosulfonate, evaluating a functional characteristic of the first and second chemically modified mutant proteins, and correlating the functional characteristic of the first and second chemically modified mutant proteins with the structures of the first and second chemically modified mutant proteins.

The chemically modified mutant proteins of the present invention provide an alternative to site-directed mutagenesis and chemical modification for introducing unnatural amino acids into proteins. Moreover, the methods of the present invention allow the preparation of pure glycoproteins (i.e., not mixtures) with predetermined and unique structures. These glycoproteins can then be used to determine structure-function relationships (e.g., structure-activity relationships ("SARs")) of non-natural variants of the proteins.

An advantage of the present invention is that it is possible to introduce predetermined glycosylation patterns into proteins in a simple and repeatable manner. This advantage provides an ability to modify critical protein characteristics such as partitioning, solubility, cell-signaling, catalytic activity, biological activity and pharmacological activity. Additionally, the methods of the present invention provide for a mechanism of "masking" certain chemically or biologically important protein sites, for example, sites which are critical for immunological or allergenic responses or sites which are critical to proteolytic degradation of the modified protein.

Another advantage of the present invention is the ability to glycosylate a protein which is not generally glycosylated, or to modify the glycosylation pattern of a protein which is generally glycosylated.

Another advantage of the present invention is improved synthetic methods for glycosylating a protein which is not generally glycosylated, or for modifying the glycosylation pattern of a protein which is generally glycosylated.

Another advantage of the present invention is novel reagents for glycosylating a protein which is not generally glycosylated, or for modifying the glycosylation pattern of a protein which is generally glycosylated.

Another advantage of the present invention is to produce enzymes that have altered catalytic activity. In one specific example, the inventors have shown that it is possible to modify the substrate specificity of a protease to increase the esterase activity as compared to the amidase activity. In another specific example, the inventors have shown that it is possible to modify the substrate specificity of a protease to increase its ability to degrade lectins. Similarly, modifications of substrate specificity would be expected when utilizing the present invention with other enzymes.

These and other advantages of the present invention are described in more detail in the following detailed description.

BRIEF DESCRIPTION OF THE DRAWINGS

FIG. 15 also illustrates an inverse addition synthesis scheme (Scheme 9) for a first generation glycodendrimer reagent.

DETAILED DESCRIPTION OF THE PREFERRED EMBODIMENTS

According to the present invention, a method is provided wherein the glycosylation pattern of a protein is modified in a predictable and repeatable manner. Generally, the modification of the protein occurs via reaction of a cysteine residue in the protein with a glycosylated thiosulfonate.

Thus, in one composition aspect of the present invention, a chemically modified mutant protein is provided, wherein said mutant protein differs from a precursor protein by virtue of having a cysteine residue substituted for a residue other than cysteine in said precursor protein, the substituted cysteine residue being subsequently modified by reacting said cysteine residue with a glycosylated thiosulfonate. Preferably, the glycosylated thiosulfonate is an alkylthiosulfonate, most preferably, a methanethiosulfonate.

In a method aspect of the present invention, a method of producing a chemically modified mutant protein is provided comprising the steps of: (a) providing a precursor protein; (b) substituting an amino acid residue other than cysteine in said precursor protein with a cysteine; (c) reacting said substituted cysteine with a glycosylated thiosulfonate, said glycosylated thiosulfonate comprising a carbohydrate moiety; and (d) obtaining a modified glycosylated protein wherein said substituted cysteine comprises a carbohydrate moiety attached thereto. Preferably, the glycosylated thiosulfonate is an alkylthiosulfonate, most preferably, a methanethiosulfonate. Also preferably, the substitution in said precursor protein is obtained by using recombinant DNA techniques by modifying a DNA encoding said precursor protein to comprise DNA encoding a cysteine at a desired location within the protein. The amino acid residues to be substituted with cysteine residues according to the present invention may be replaced using site-directed mutagenesis methods or other methods well known in the art. See, for example, PCT Publication No. WO 95/10615, which is hereby incorporated by reference.

The present invention also relates to glycosylated thiosulfonate. Preferably, the glycosylated thiosulfonate comprises methanethiosulfonate. More preferably, the methanethiosulfonate comprises the chemical structure:

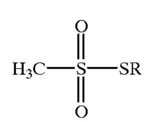

where R comprises -β-Glc, -Et-β-Gal, -Et-β-Glc, -Et-α-Glc, -Et-α-Man, -Et-Lac, -β-Glc$(Ac)_2$, -β-Glc$(Ac)_3$, -β-Glc$(Ac)_4$, -Et-α-Glc$(Ac)_2$, -Et-α-Glc$(Ac)_3$, -Et-α-Glc$(Ac)_4$, -Et-β-Glc$(AC)_2$, -Et-β-Glc$(Ac)_3$, -Et-β-Glc$(Ac)_4$, -Et-α-Man $(Ac)_3$, -Et-α-Man$(AC)_4$, -Et-β-Gal$(Ac)_3$, -Et-β-Gal $(Ac)_4$, -Et-Lac$(Ac)_5$, -Et-Lac$(Ac)_6$, -Et-Lac$(AC)_7$.

Another aspect of the present invention is a method of modifying the functional characteristics of a protein including providing a protein and reacting the protein with a glycosylated thiosulfonate reagent under conditions effective to produce a glycoprotein with altered functional characteristics as compared to the protein.

The functional characteristics of a protein which may be altered by the present invention include, but are not limited to, enzymatic activity, the effect on a human or animal body, the ability to act as a vaccine, the tertiary structure (i.e., how the protein folds), whether it is allergenic, its solubility, its signaling effects, its biological activity and its pharmacological activity (Paulson, "Glycoproteins: What are the sugar chains for?" *Trends in Biochem. Sciences,* 14:272–276 (1989), which is hereby incorporated by reference). The use of glycosylated thiosulfonates as thiol-specific modifying reagents in a method of the present invention allows virtually unlimited alterations of protein residues. In addition, this method allows the production of pure glycoproteins with predetermined and unique structures and therefore, unique functional characteristics, with control over both the site and level of glycosylation.

In particular, the methods of modifying the functional characteristics of a protein allow the preparation of single glycoforms through regio- and glycan-specific protein glycosylation at predetermined sites. Such advantages provide an array of options with respect to modification of protein properties which did not exist in the prior art. The ability to produce proteins having very specific and predictable glycosylation patterns enables production of proteins that have known and quantifiable effects in chemical, pharmaceutical, immunological, or catalytic performance. For example, with knowledge of a specific problematic epitope, it is possible to construct a modified protein according to the present invention in which the epitope is masked by a carbohydrate moiety, thus reducing its allergenic or immunogenic response in a subject. As another example, where the solubility of a protein is problematic in terms of recovery or formulation in a pharmaceutical or industrial application, it is possible, utilizing the present invention, to produce a protein that has altered solubility profiles thus producing a more desirable protein product. As another example, if a protein has a particular problem of being proteolytically unstable in the environment in which it is to be used, then it is possible to mask the proteolytic cleavage sites in the protein using the present invention to cover up such sites with a carbohydrate moiety. These examples are merely a few of the many applications of the present invention to produce improved proteins.

Accordingly, the present invention provides for modified protein, wherein the protein comprises a wholly or partially predetermined glycosylation pattern which differs from the glycosylation pattern of the protein in its precursor, natural, or wild type state and a method for producing such a modified protein. As used herein, glycosylation pattern means the composition of a carbohydrate moiety. The present invention also relates to methods of determining the structure-function relationships of chemically modified mutant proteins. The first method includes providing first and second chemically modified mutant proteins of the present invention, wherein the glycosylation pattern of the second chemically modified mutant protein differs from the glycosylation pattern of the first chemically modified mutant protein, evaluating a functional characteristic of the first and second chemically modified mutant proteins, and correlating the functional characteristic of the first and second chemically modified mutant proteins with the structures of the first and second chemically modified mutant proteins. The second method involves providing a first and second chemically modified mutant protein of the present invention, wherein at least one different cysteine residue in the second chemically modified mutant protein is modified by reacting said cysteine residue with a glycosylated thiosulfonate evaluating a functional characteristic of the first and second chemically modified mutant proteins, and correlating the functional characteristic of the first and second chemically modified mutant proteins with the structures of the first and second chemically modified mutant proteins.

Figure 1:
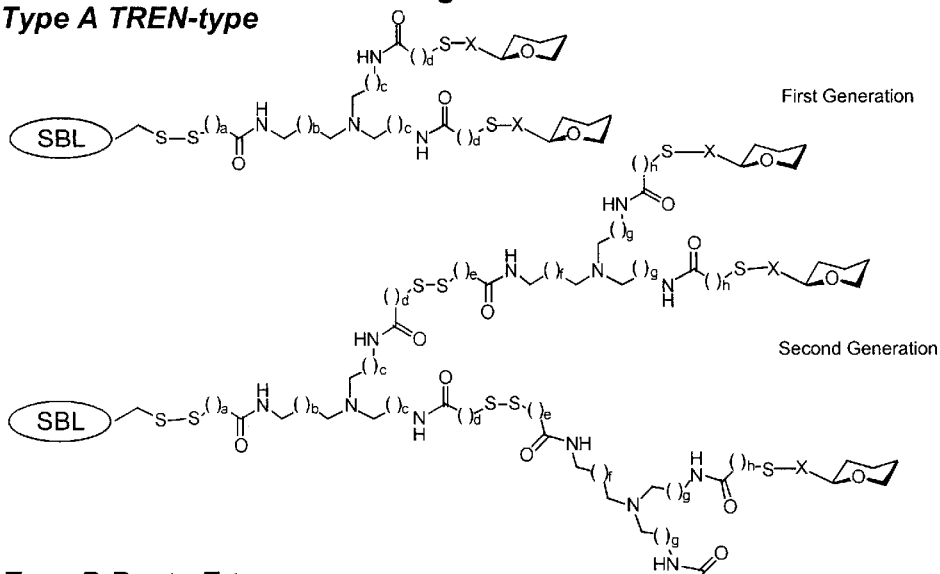
FIG. 1 shows dendrimer methanethiosulfonate ("MTS") reagents.
Figure 1:
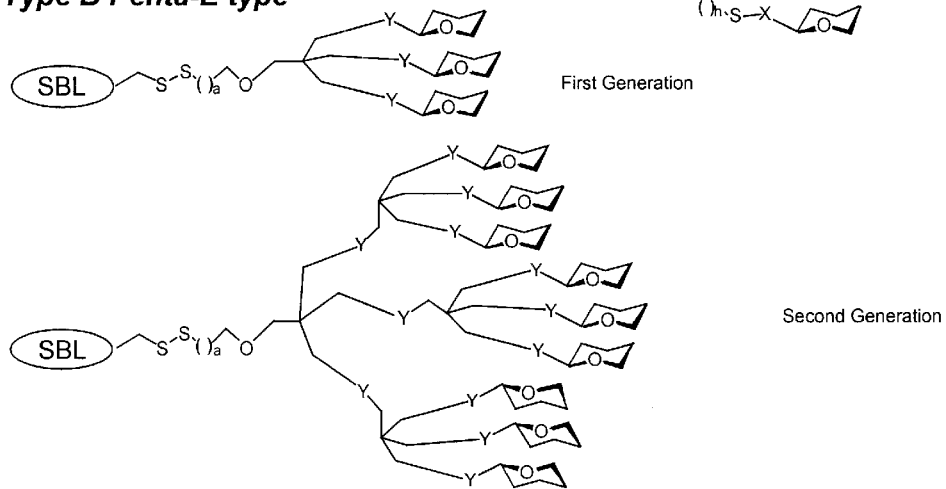
Figure 1:
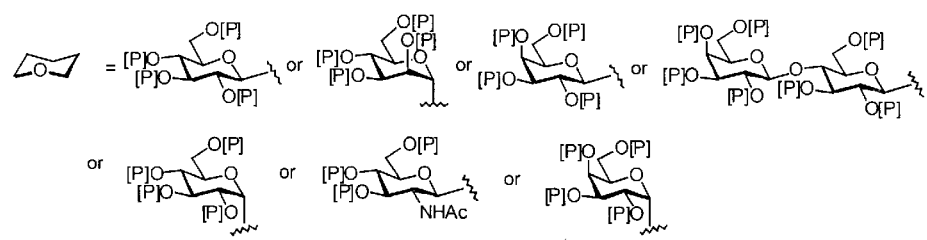

The chemically modified mutant proteins of the present invention provide a valuable source of carbohydrate-protein conjugates. Moreover, the methods of the present invention allow the preparation of pure glycoproteins (i.e., not mixtures) with predetermined and unique structures. These glycoproteins can then be used to determine structure-function relationships (e.g., structure-activity relationships ("SARs")) of non-natural variants of the proteins.

The protein of the invention may be any protein for which a modification of the glycosylation pattern thereof may be desirable. For example, proteins which are naturally not glycosylated may be glycosylated via the invention. Similarly, proteins which exist in a a naturally glycosylated form may be modified so that the glycosylation pattern confers improved or desirable properties to the protein. Specifically, proteins useful in the present invention are those in which glycosylation plays a role in functional characteristics such as, for example, biological activity, chemical activity, pharmacological activity, or immunological activity.

Glycosylated proteins as referred to herein means moieties having carbohydrate components which are present on proteins, peptides, or amino acids. In the present invention, the glycosylation is provided, for example, as a result of reaction of the glycosylated thiosulfonate with the thiol hydrogen of a cysteine residue thereby producing an amino acid residue which has bound thereto the carbohydrate component present on the glycosylated thiosulfonate. Glycosylation also may be accomplished, according to the present invention, by attachment of glycodendrimer reagents such as those described in the examples below. Such reagents comprise one or more dendrimer core portions, optionally a linker (or tether), and one or more carbohydrate moieties.

The invention provides for synthetic schemes for producing glycodendrimer reagents. Said schemes include normal addition schemes in which a carbohydrate alkylthiosulfonate is reacted with a dendrimer core, said core comprising a free sulfhydryl group. Also included are inverse addition synthesis schemes in which a thioglycose is reacted with a dendrimer core alkylthiosulfonate. Further included are synthesis schemes for producing novel carbohydrate alkylthiosulfonates, including direct linked and tethered carbohydrate alkylthiosulfonates. A preferred synthesis scheme involves reacting a carbohydrate with an alkylthiosulfonate and a phase transfer catalyst under refluxing toluene conditions. In a particularly preferred scheme, the alkylthiosulfonate is a sodium salt of methanethiosulfonate, and the phase transfer catalyst is tetrabutylammonium iodide ($Bu_4NI$).

In a preferred embodiment, the protein is an enzyme. The term "enzyme" includes proteins that are capable of catalyzing chemical changes in other substances without being changed themselves. The enzymes can be wild-type enzymes or variant enzymes. Enzymes within the scope of the present invention include pullulanases, proteases, cellulases, amylases, isomerases, lipases, oxidases, and reductases. Preferably, the enzyme is a protease. Wild-type enzyme can be a wild-type or mutant protease. Wild-type proteases can be isolated from, for example, *Bacillus lentus* or *Bacillus amyloliquefaciens* (also referred to as BPN'). Mutant proteases can be made according to the teachings of, for example, PCT Publication Nos. WO 95/10615 and WO 91/06637, which are hereby incorporated by reference. Functional characteristics of enzymes which are suitable for modification according to the present invention include, for example, enzymatic activity, solubility, partitioning, cell—cell signaling, substrate specificity, substrate binding, stability to temperature and reagents, ability to mask an antigenic site, physiological functions, and pharmaceutical functions (Paulson, "Glycoproteins: What are the Sugar Chains For?" *Trends in Biochem Sciences*, 14:272–276 (1989), which is hereby incorporated by reference.)

In a preferred embodiment the protein is modified so that a non-cysteine residue is substituted with a cysteine residue, preferably by recombinant means. Preferably, the amino acids replaced in the protein by cysteine are selected from the group consisting of asparagine, leucine or serine. Orthogonal protection schemes that are well known in the art may be used when modification is to be carried out at more than one site within a protein.

The terms "thiol side chain group," "thiol containing group," and "thiol side chain" are terms which can be used interchangeably and include groups that are used to replace the thiol hydrogen of a cysteine. In certain embodiments, the cysteine occurs in the native protein sequence, while in other embodiments, a cysteine replaces one or more amino acids in the protein. Commonly, the thiol side chain group includes a sulfur through which the thiol side chain groups defined above are attached to the thiol sulfur of the cysteine.

The glycosylated thiosulfonates of the invention are those which are capable of reacting with a thiol hydrogen of a cysteine to produce a glycosylated amino acid residue. By glycosylated is meant that the thiosulfonate has bound thereto a sugar or carbohydrate moiety that can be transferred to a protein or dendrimer (which may be bound to a protein) pursuant to the present invention. Preferably, the glycosylated thiosulfonates are glycosylated alkylthiosulfonates, most preferably, glycosylated methanethiosulfonates. Such glycosylated methanethiosulfonates have the general formula:

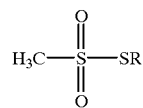

In particularly preferred embodiments, the methanethiosulfonate R group comprises: -β-Glc, -Et-β-Gal, -Et-β-Glc, -Et-α-Glc, -Et-α-Man, -Et-Lac, -β-Glc(Ac)$_2$, -β-Glc(Ac)$_3$, -β-Glc(Ac)$_4$, -Et-α-Glc(Ac)$_2$, -Et-α-Glc(Ac)$_3$, -Et-α-Glc(Ac)$_4$, -Et-β-Glc(Ac)$_2$, -Et-β-Glc(Ac)$_3$, -Et-β-Glc(Ac)$_4$, -Et-α-Man(Ac)$_3$, -Et-α-Man(Ac)$_4$, -Et-β-Gal(Ac)$_3$, -Et-β-Gal(Ac)$_4$, -Et-Lac(Ac)$_5$, -Et-Lac(Ac)$_6$, -Et-Lac(Ac)$_7$.

In a preferred embodiment, the carbohydrate moiety of the present invention is a dendrimer moiety. Multiple functionalization of chemically modified mutant proteins can be achieved by dendrimer approaches, whereby multiple-branched linking structures can be employed to create poly-functionalized chemically modified mutant proteins.

Highly branched molecules or dendrimers first were synthesized by Vögtle in 1978 (Buhleier et al., *Synthesis*, 155–158 (1978), which is hereby incorporated by reference). The attachment of identical building blocks that contain branching sites to a central core may be achieved with a high degree of homogeneity and control. Each branch contains a functional group which, after chemical alteration, may be connected to yet another branching building block. In this manner, layer after layer of branching rapidly generates highly-functionalized molecules.

Figure 12:
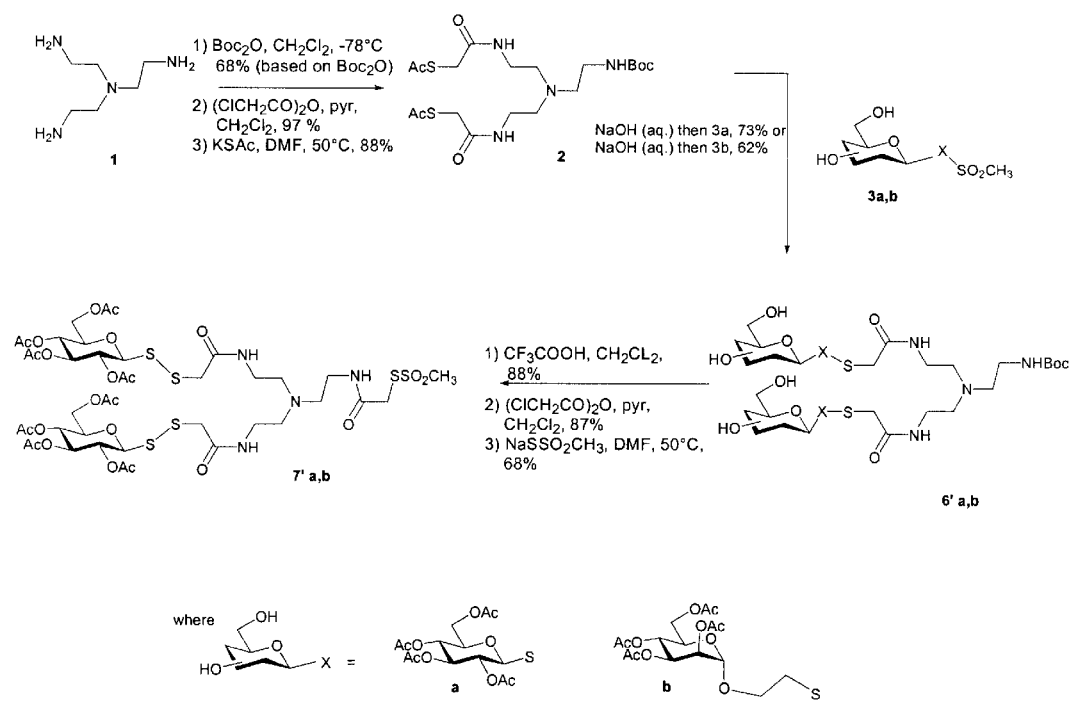
FIG. 12 shows a normal addition synthetic scheme for producing two different first-generation Type A glycodendrimer MTS reagents, and glycodendriproteins produced from these reagents.
Figure 12:
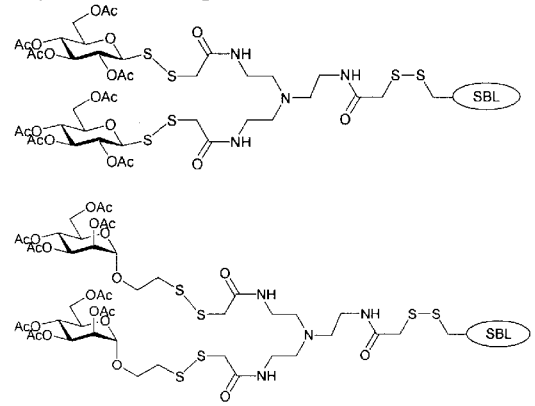
Figure 14:
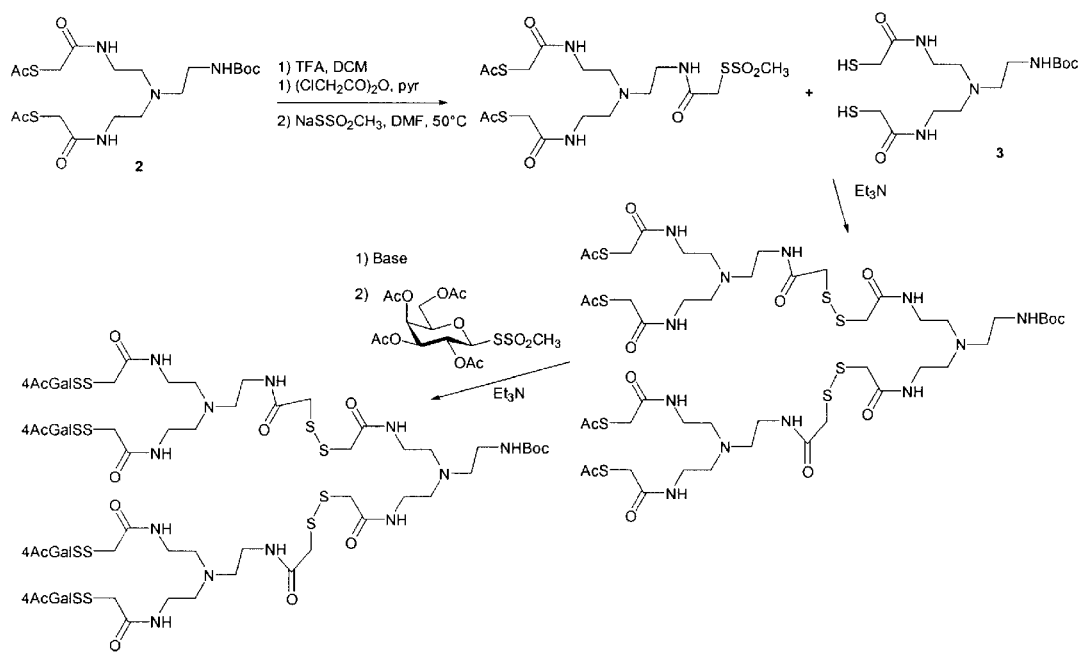
FIG. 14 shows a normal addition synthetic scheme for producing a second generation Type A glycodendrimer reagent.

For instance, multiple glycosylation, including multiple mannose-containing chemically modified mutant proteins, and varied sugar moieties can be created. The dendrimer reagent structures would include methanethiosulfonates with simple branching such as:

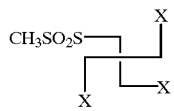

derived from pentaerythritol (i.e., "Penta-E"), to very complex branched dendrimer reagents (see FIG. 1). In particular, a first generation glycodendrimer reagent is synthesized as shown in FIG. 12, Scheme 6. This approach can be extended to cover larger dendrimers. More specifically, by leaving one "arm" of the glycodendrimer free for conversion to a methanethiosulfonate, the remaining arms can be further branched to synthesize highly-functionalized glycodendrimer reagents as shown in FIG. 14, Scheme 8.

Figure 5:
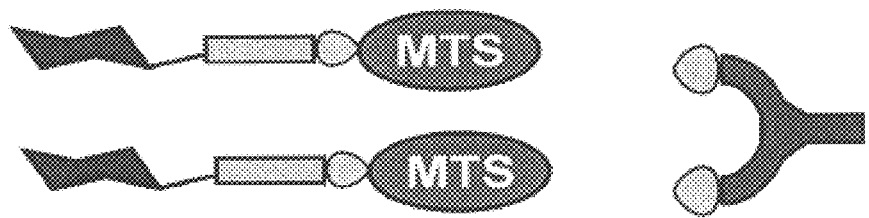
FIG. 5 shows two different synthetic approaches for generating glycodendrimers, i.e., normal addition, and inverse addition.
Figure 5:
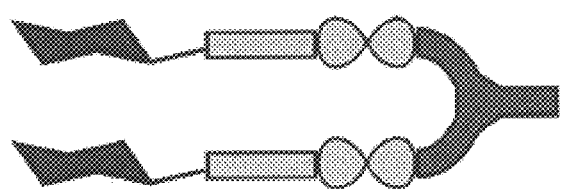
Figure 5:
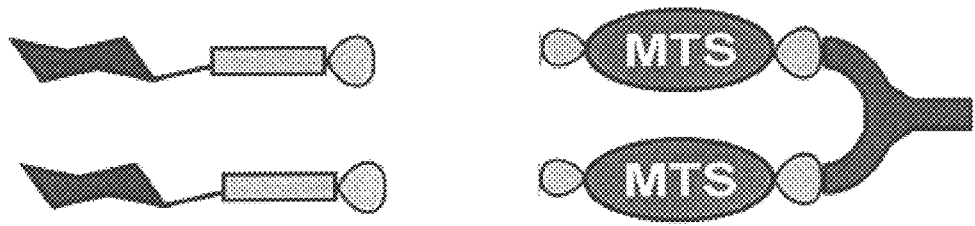
Figure 5:
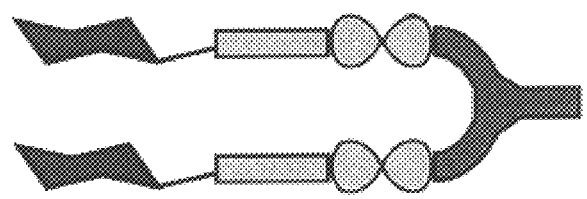

By way of example to illustrate some of its advantages, the following discussion will focus on certain proteases which are modified according to the methods of the present invention. Alkaline serine proteases (subtilisins) are finding increasing use in biocatalysis, particularly in chiral resolution, regioselective acylation of polyfunctional compounds, peptide coupling, and glycopeptide synthesis. As shown in FIG. 5 of U.S. patent application Ser. No. 09/347,029, subtilisins can catalyze peptide bond formation starting from an ester substrate, by first forming an acyl enzyme intermediate which then reacts with a primary amine to form the peptide product. This application requires high esterase activity to promote acyl enzyme formation and low amidase activity to minimize hydrolysis of the peptide bond of the desired product. Generally, subtilisins do not meet these requirements. However, the improvement of the esterase to amidase selectivities of subtilisins has been a long sought after goal. By using the methods provided for in the present invention, it is possible to produce subtilisins that have advantageous properties.

The inventors in the present case used site specific mutagenesis to modify certain residues and introduce additional cysteine residues within subtilisin which would then serve to react with a glycosylated methanethiosulfonate or glycodendrimer reagent to produce a glycosylation point at the introduced cysteine. *Bacillus lentus* subtilisin was selected for illustrated purposes because it does not contain a natural cysteine and is not naturally glycosylated.

The substrate binding site of an enzyme consists of a series of subsites across the surface of the enzyme. The portion of substrate that corresponds to the subsites are labeled P and the subsites are labeled S. By convention, the subsites are labeled $S_1$, $S_2$, $S_3$, $S_1'$, and $S_2'$. A discussion of subsites can be found in Berger et al., *Phil Trans. Royl Soc. Lond. B.* 257:249–264 (1970), Siezen et al., *Protein Engineering*, 4:719–737 (1991), and Fersht, *Enzyme Structure and Mechanism*, 2 ed., Freeman: New York, 29–30 (1985), which are hereby incorporated by reference.

In the present illustration, the $S_1$, $S_1'$, or $S_2$ subsites were selected as suitable targets for modification. In particular, the amino acids corresponding to N62, L217, S156, and S166 in naturally-occurring subtilisin from *Bacillus amyloliquefaciens* or to equivalent amino acid residues in other subtilisins, such as *Bacillus lentus* subtilisin were selected for modification to cysteine.

A residue (amino acid) of an enzyme is equivalent to a residue of a referenced enzyme (e.g., *B. amyloliquefaciens* subtilisin) if it is either homologous (i.e., corresponding in position in either primary or tertiary structure) or analogous to a specific residue or portion of that residue in *B. amyloliquefaciens* subtilisin (i.e., having the same or similar functional capacity to combine, react, or interact chemically).

To establish homology to primary structure, the amino acid sequence of the subject enzyme (e.g., a serine hydrolase, cysteine protease, aspartyl protease, metalloprotease, etc.) is directly compared to a reference enzyme (e.g., *B. amyloliquefaciens* subtilisin in the case of a subtilisin type serine protease) primary sequence and particularly to a set of residues known to be invariant in all enzymes of that family (e.g. subtilisins) for which sequence is known. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of the reference enzyme (e.g., *B. amyloliquefaciens* subtilisin) are defined. Alignment of conserved residues preferably should conserve 100% of such residues. However, alignment of greater than 75% or as little as 50% of conserved residues is also adequate to define equivalent residues. Conservation of the catalytic triad, (e.g., Asp32/His64/Ser221) should be maintained for serine hydrolases.

Figure 2:
FIG. 2 shows dendrimer methanethiosulfonate ("MTS") reagents and hybrid dendrimer methanethiosulfonate ("MTS") reagents.
Figure 2:
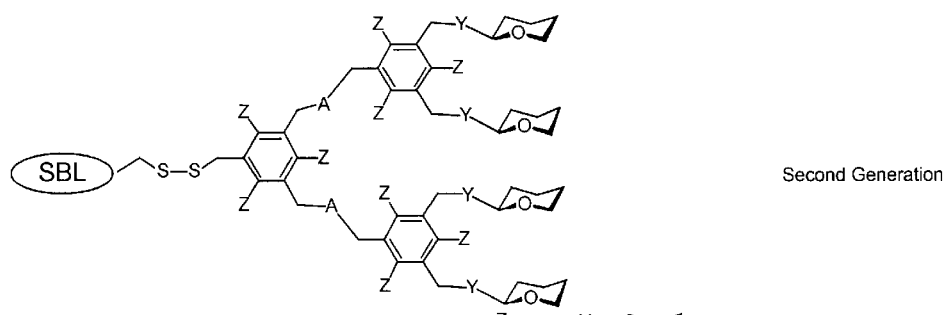
Figure 2:
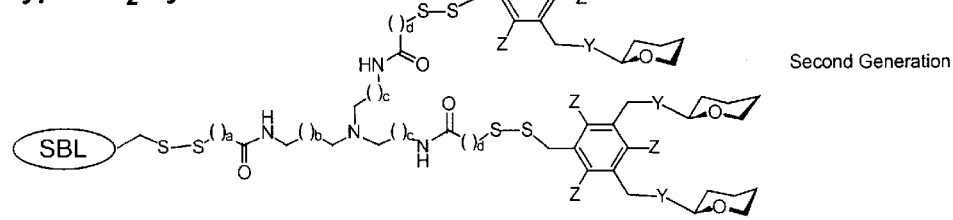
Figure 2:
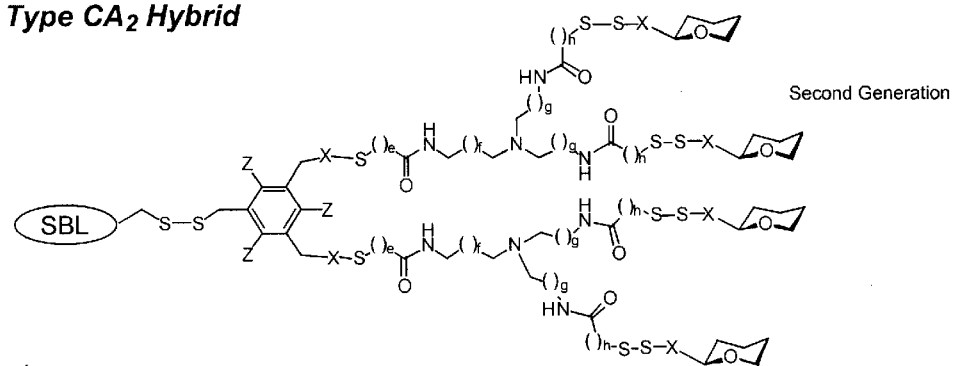
Figure 2:
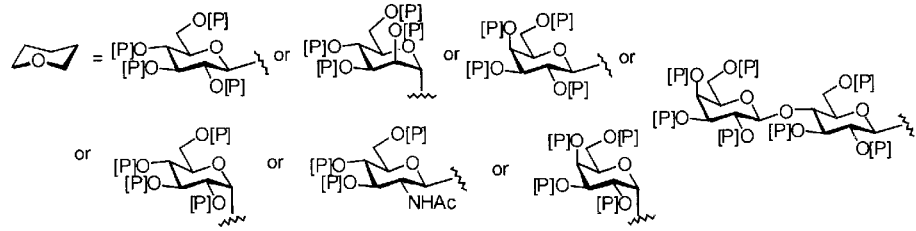

The conserved residues may be used to define the corresponding equivalent amino acid residues in other related enzymes. For example, the two ("reference" and "target") sequences are aligned in order to produce the maximum homology of conserved residues. There may be a number of insertions and deletions in the "target" sequence as compared to the "reference" sequence. Thus, for example, a number of deletions are seen in the thermitase sequence as compared to *B. amyloliquefaciens* subtilisin (see, e.g. U.S. Pat. No. 5,972,682). Thus, the equivalent amino acid of Tyr217 in *B. amyloliquefaciens* subtilisin in thermitase is the particular lysine shown beneath Tyr217 in FIGS. 5B–2 of the U.S. Pat. No. 5,972,682 patent.

The particular "equivalent" resides may be substituted by a different amino acid to produce a mutant carbonyl hydrolase since they are equivalent in primary structure.

Equivalent residues homologous at the level of tertiary structure for a particular enzyme whose tertiary structure has been determined by x-ray crystallography, are defined as those for which the atomic coordinates of 2 or more of the main chain atoms of a particular amino acid residue of the reference sequence (e.g., *B. amyloliquefaciens* subtilisin) and the sequence in question (target sequence) (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the enzyme in question to the reference sequence. The best model is the crystallographic model giving the lowest R factor for experimental diffraction data at the highest resolution available.

$$R = \frac{\sum_h |Fo(h)| - |Fc(h)|}{\sum_h |Fo(h)|}$$

Equivalent residues which are functionally analogous to a specific residue of a reference sequence (e.g., *B. amyloliquefaciens* subtilisin) are defined as those amino acids sequence in question (e.g., in a related subtilisin) which may adopt a conformation such that they will alter, modify or contribute to protein structure, substrate binding or catalysis in a manner defined and attributed to a specific residue of the reference sequence as described herein. Further, they are those residues of the sequence in question (for which a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of the reference sequence residue(s). The three dimensional structures would be aligned as outlined above. For an illustration of this procedure see U.S. Pat. No. 5,972,682.

The mutated subtilisins were produced through standard site directed mutagenesis techniques and the obtained mutant subtilisin was reacted with certain glycosylated alkylthiosulfonates, particularly glycosylated methanethiosulfonates, as provided in the examples appended hereto.

Proteins obtained using the methods provided herein may be used in any application in which it is desired to use such proteins, where having modified functional capabilities is advantageous. Thus proteins modified as provided herein may be used in the medical field for pharmaceutical compositions and in diagnostic preparations.

Additionally, proteins such as enzymes that are modified according to the present invention may be used in applications which generally are known for such enzymes including industrial applications such as cleaning products, textile processing, feed modification, food modification, brewing of grain beverages, starch processing, as antimicrobials, and in personal care formulations. Moreover, the unique functionalities made possible by the present invention may result in uses for proteins which have not heretofore been recognized as feasible.

EXAMPLES

Example 1

Synthesis and Characterization of Carbohydrate Methanethiosulfonate Reagents

Various carbohydrate-methanethiosulfonates have been prepared previously, as described in U.S. patent application Ser. No. 09/347,029 "Chemically Modified Proteins with a Carbohydrate Moiety," the entire disclosure of which is hereby incorporated by reference in its entirety. The following examples are those that have been re-prepared or prepared as novel compounds for use in glycodendriproteins.

Figure 6:
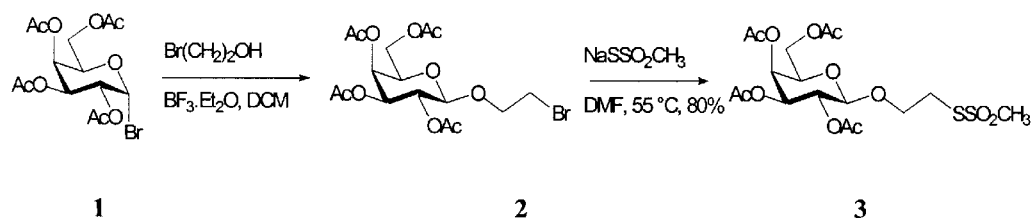
FIG. 6 shows several synthetic schemes for generating tethered and direct-linked carbohydrate MTS reagents.
Figure 6:
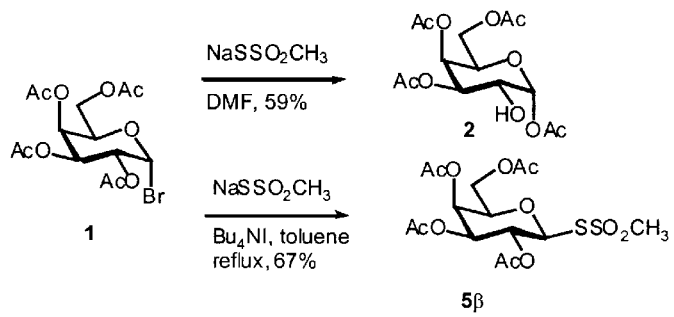
Figure 6:
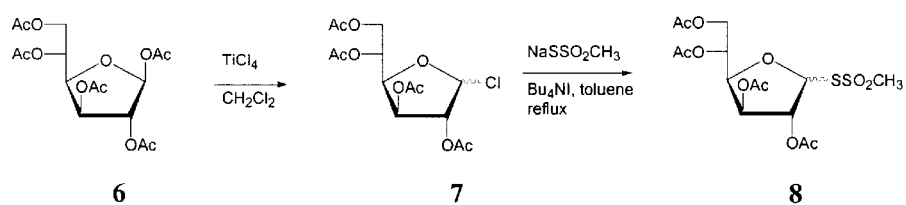

The sugar-MTS reagents required for attachment to the tips of the dendrimer were prepared. 2-(2,3,4,6-Tetra-O-acetyl-β-D-galactopyranosyl)ethyl methanethiosulfonate 3 was prepared as previously described (FIG. 6, Scheme 1). (Davis, B. G.; Maughan, M. A. T.; Green, M. P.; Ullman, A.; Jones, J. B. Tetrahedron Asymm. 2000, 11, 245).

The corresponding directly linked methanethiosulfonate 5β was unknown and a synthesis needed to be developed. DMF has been used with limited success for the synthesis of other directly linked methanethiosulfonates. These reaction conditions were tried for the reaction of 1 with sodium methanethiosulfonate. (FIG. 6, Scheme 2). A nicely crystalline product was obtained in high yield, but unfortunately, it was the acetyl migration, hydrolysis product 2. This is a known compound and was identified by comparison with the literature. Chittenden, G. J. F. Carbohydr. Res. 1988, 183, 140.

Figure 8:
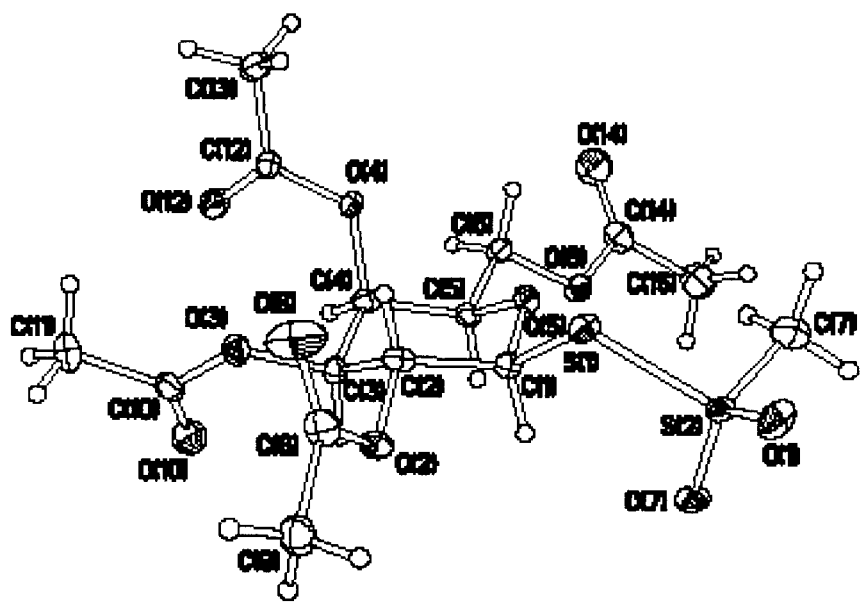
FIG. 8 shows the X-ray crystal structure of the MTS reagent 5β.
Figure 8:
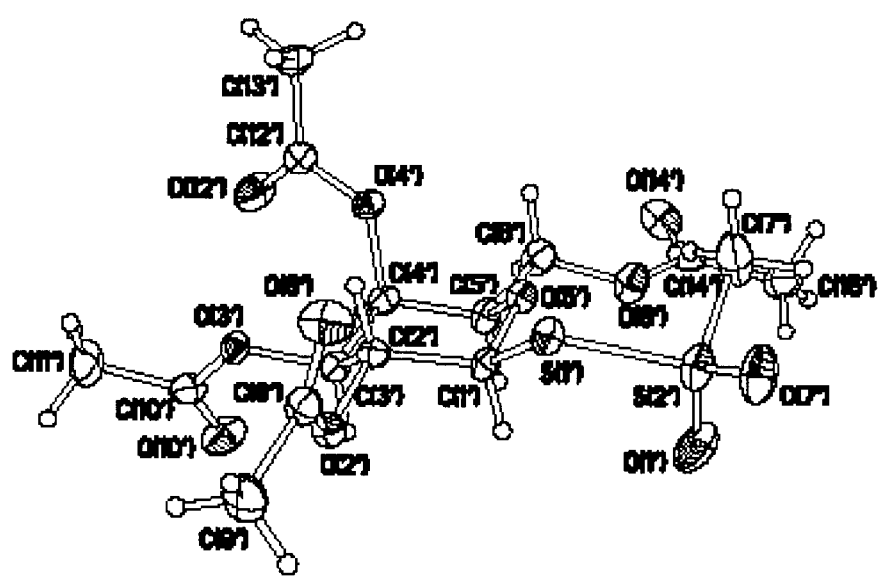

The reaction of 1 with sodium methanethiosulfonate was attempted in refluxing toluene. Very little reaction occurs but all reagents appear to be stable under these conditions. A phase transfer catalyst (tetrabutylammonium iodide) was added to increase the solubility of the methanethiosulfonate salt. This gave 5β in 67% yield after chromatography (FIG. 6, Scheme 2). Tetrabutylammonium salts of thiols have previously been used to synthesise α-thiogalactosides from the β-chloride. Blanc-Muesser, M.; Vigne, L.; Driguez, H. Terahedron Lett. 1990, 31 (27), 3869. There was initial uncertainty over the anomeric configuration of MTS reagent 5β C1-H1 NMR coupling suggested that the product was alpha anomeric stereochemistry ($^1J_1CH=165$ Hz), (Bock, K.; Pedersen, C. J. Chem. Soc., Perkin Trans. 11974, 293) but X-ray crystallography determined the absolute configuration to be the β-anomer. There are two molecules in the unit cell (FIG. 8). Details of the X-ray structure are given in the experimental section.

MTS reagent 3 could also be prepared from 2 using this tetrabutylammonium method, but the yields and rate were no improvement on that described in Scheme 1. This method was also used to prepare the directly linked glucofuranosyl MTS reagent 8 (FIG. 6, Scheme 3). The product was an inseparable anomeric mixture. No further effort has yet been made to obtain pure 8α, or 8β. Glucofuranose 6 the first readily available crystalline peracylated glucofuranose. Furneaux, R. H.; Rendle, P. M.; Sims, I. M. J Chem. Soc., Perkin Trans. 12000, 2011. Glucose generally occurs in the pyranose form and glucofuranoses are very rarely, if ever seen naturally. Synthesis of 8 would allow a route to the addition of a readily available, non-natural sugar to a protein or glycodendriprotein. Others have been investigating the preparation of furanosyl donors for this purpose. Ferrieres, V.; Bertho, J.-N.; Plusquellec, D. Carbohydr. Res. 1998, 311, 25.

Figure 7:
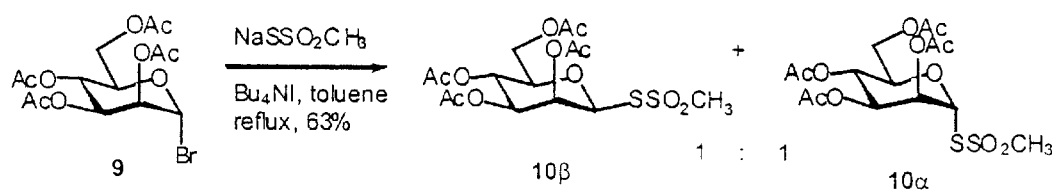
FIG. 7 shows additional synthetic schemes for generating direct-linked carbohydrate MTS reagents.
Figure 7:
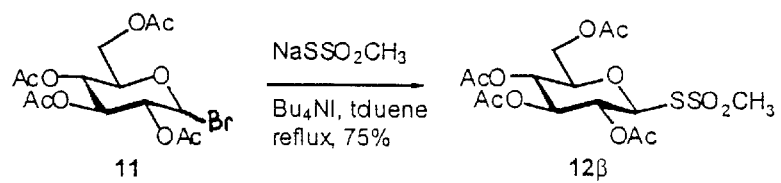
Figure 9:
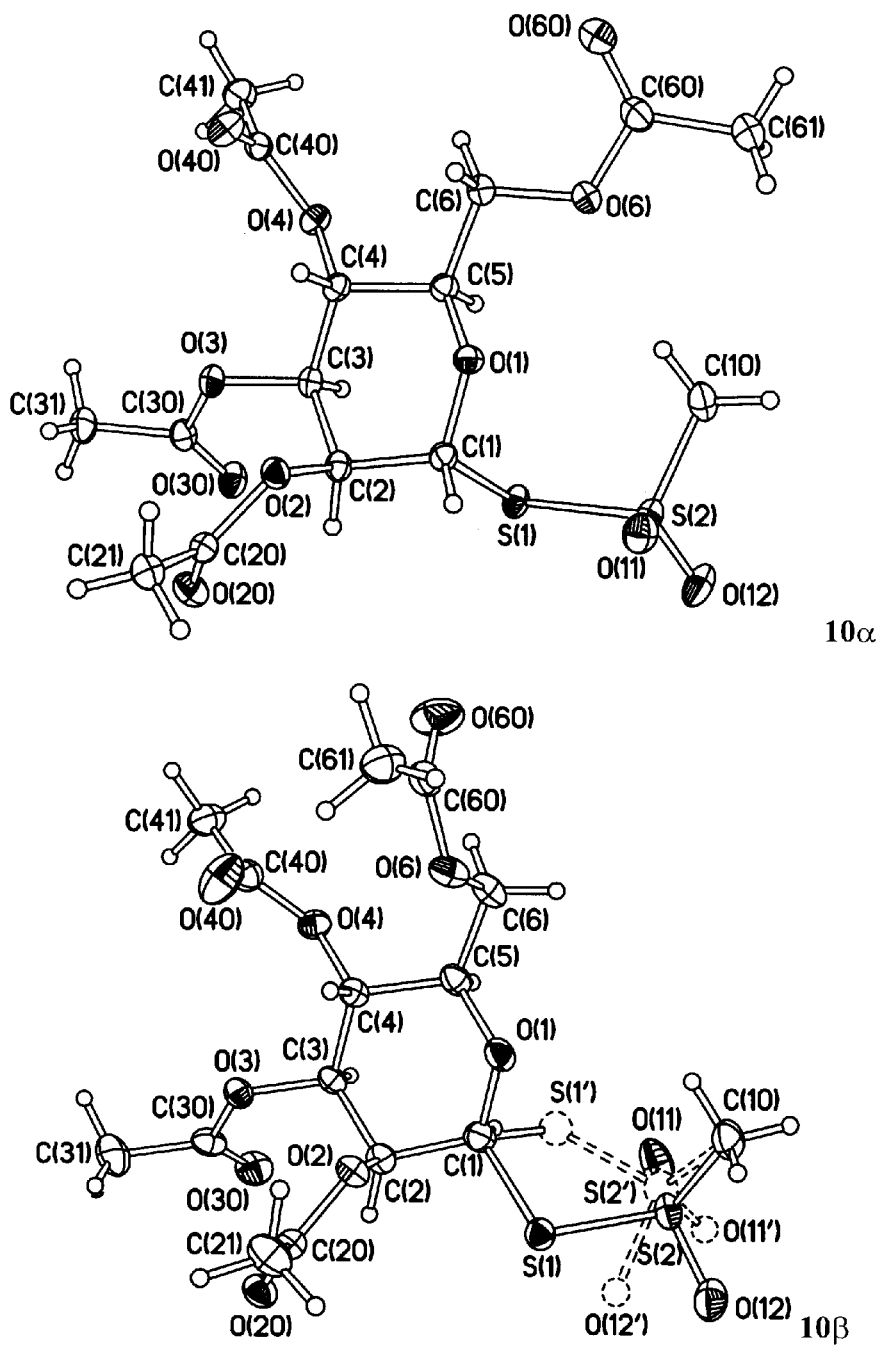
FIG. 9 shows the X-ray crystal structure of the MTS reagents 10α and 10β.

This method has also allowed the preparation of novel directly-linked mannose MTS reagents 10α and 10β (FIG. 7, Scheme 4), whose identity was again confirmed by X-ray crystallography (FIG. 9). In addition it allowed the more efficient preparation of β-gluco MTS reagent 12β (FIG. 7, Scheme 5).

Experimental 2,3,4,6-Tetra-O-acetyl-β-D-galactopyranosyl methanethiosulfonate 5β

Acetobromogalactose 1 (1.1 g, 2.68 mmol) and sodium methanethiosulfonate (0.45 g, 3.35 mmol) in toluene (50 mL) were concentrated in vacuo to approximately 30 mL to remove any water as the azeotrope. The mixture was made up to 50 mL with more toluene and again concentrated to 30 mL. A catalytic amount of tetrabutylammonium iodide was added and the mixture heated at reflux for 75 minutes. After cooling, Celite (to stop the formation of a salt cake on top of the column) was added and the whole mixture loaded directly on to a flash silica column. Elution with 40% ethyl acetate in petroleum ether and recrystallization from petroleum ether/ethyl acetate gave the title compound (787 mg, 67%) as colorless prisms; mp 118–119° C. (petroleum ether/ethyl acetate); $[\alpha]_{23}^D$=+8.5 (c 1.0, CHCl$_3$); IR (KBr) 1753 (C=O), 1325, 1138 (S—SO$_2$) cm$^{-1}$; $^1$H NMR (400 MHz, CDCl$_3$) δ 1.99 (s, 3H, Ac), 2.50 (s, 3H, Ac), 2.08 (s, 3H, Ac), 2.17 (s, 3H, Ac), 3.43 (s, 3H, CH$_3$SO$_2$—), 4.05 (ddd, J 7.4, 4.2, 0.9 Hz, 1 H), 4.08 (dd, J 18.3, 7.5 Hz, 1H), 4.20 (dd, J 10.8, 4.3 Hz, 1H), 5.13 (dtd, J 10.7, 7.6, 3.4 Hz, 1H), 5.26 (s, 1H), 5.27 (dd, J 14.8, 10.3 Hz, 1H), 5.48 (dd, J 3.4, 0.8 Hz, 1H); $^{13}$C NMR (100 MHz, CDCl$_3$) δ 20.5, 20.6, 20.6, 20.6 (4×CH$_3$CO), 52.7 (CH$_3$SO$_2$—), 61.8 (C-6), 65.8, 67.0, 71.3, 75.3, 87.0 ($^1J_1$CH 165 Hz, C-1), 169.7, 169.7, 170.0, 170.2 (4×C=O); HRMS m/z (ES): found 460.0951; $C_{15}H_{26}NO_{11}S_2$ requires 460.0947.

TABLE 1

Crystal data and structure refinement for
2,3,4,6-Tetra-O-acetyl-β-D-
galactopyranosyl methanethiosulfonate 5β.

| | |
|---|---|
| Identification code | 00srv327 |
| Empirical formula | C15 H22 O11 S2 |
| Formula weight | 442.45 |
| Temperature | 102(2) K |
| Wavelength | 0.71073 Å |
| Crystal system | Orthorhombic |
| Space group | $P2_12_12_1$ (No. 19) |
| Unit cell dimensions | a = 9.279(4) Å |
| α = 90° | |
| | b = 9.314(5) Å |
| β = 90° | |
| | c = 47.04(2) Å |
| γ = 90° | |
| Volume | 4065(3) Å$^3$ |
| Z | 8 |
| Density (calculated) | 1.446 g/cm$^3$ |
| Absorption coefficient | 0.316 mm$^{-1}$ |
| F(000) | 1856 |
| Crystal size | 0.35 × 0.5 × 0.6 mm$^3$ |
| θ range for data collection | 1.73 to 29.00°. |
| Index ranges | −12 ≤ h ≤ 12, −12 ≤ k ≤ 6, −56 ≤ l ≤ 41 |
| Reflections collected | 23902 |
| Independent reflections | 9150 [R(int) = 0.0394] |
| Reflections with I > 2σ(I) | 8973 |
| Completeness to θ = 29.00° | 86.5% |
| Absorption correction | None |
| Refinement method | Full-matrix least-squares on F$^2$ |
| Data/restraints/parameters | 9150/0/525 |
| Largest final shift/e.s.d. ratio | 0.033 |
| Goodness-of-fit on F$^2$ | 1.176 |
| Final R indices [I > 2σ(I)] | R1 = 0.0428, wR2 = 0.1063 |
| R indices (all data) | R1 = 0.0438, wR2 = 0.1069 |
| Absolute structure parameter | 0.04(6) |
| Largest diff. peak and hole | 0.542 and −0.378 e.Å$^{-3}$ |

2,3,4,6-Tetra-O-acetyl-α-mannopyranosylmethanethiosulfonate 10α and 2,3,4,6-Tetra-O-acetyl-β-D-mannopyranosylmethanethiosulfonate 10β

The title compounds were prepared using essentially the same method as described above. Minor modifications to this method were made so that the silica plug mixture was purified using Flash silica column with eluting solvent 70:30 Petroleum Ether: Ethyl Acetate, moving to 60:40 Petroleum Ether: Ethyl Acetate. This separated α/β mixture from the remaining bromide but two anomers could not be separated on the column. This was achieved through several recrystallizations from petroleum ether/Ethyl Acetate. The two anomers are recovered off the column in a 50:50 mixture. The β anomer crystallizes first. The α anomer eventually crystallizes to give pure crystals. Yield=63%.

2,3,4,6-Tetra-O-acetyl-β-D-glucopyranosyl methanethiosulfonate 12β

2,3,4,6-Tetra-O-acetyl-α-D-glucopyranosyl bromide (1 g, 2.44 mmol) and sodium methanethiosulfonate (0.4 g, 3.05 mmol) were placed under nitrogen. 30 ml of anhydrous toluene was added followed by tetrabutylammonium bromide (69 mg, 0.21 mmol) and the mixture heated under reflux for 75 minutes. Part way through 6 ml of DMF were added as it seemed that 2,3,4,6-Tetra-O-acetyl-α-D-glucopyranosyl bromide was insoluble in toluene. Reaction continued to reflux despite the fact that solution not formed. Thin Layer Chromatography ("TLC") at end of reaction showed reaction to have gone to completion. Solution reduced on high pressure rotary evaporator to remove DMF. Product purified on flash silica gel column, reaction mixture added directly onto column (adding a small amount of Celite to reaction mixture sufficient to avoid salt cake forming on top of column.) Petroleum Ether: Ethyl Acetate 60:40 was used as the eluting solvent. Yield=75%.

Example 2

TREN-based (Type A) Glycodendrimer Synthesis
Introduction

Figure 3:
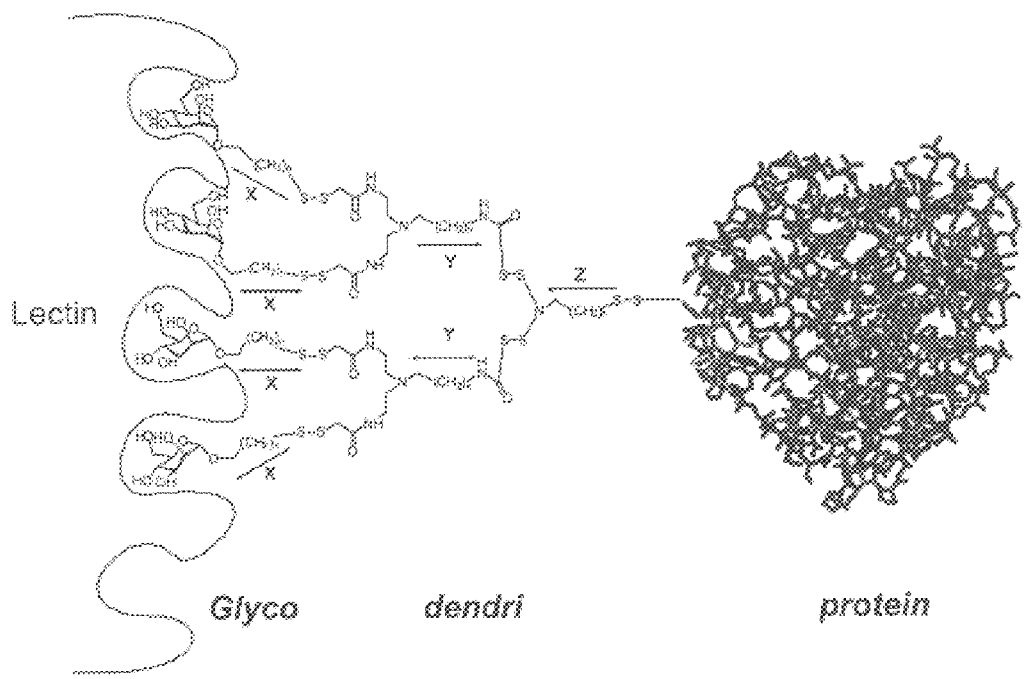
FIG. 3 shows a glycodendrimer protein binding to carbohydrate binding sites on a lectin. X, Y and Z represent optional carbohydrate linkers; the lengths of these linkers, if present, need not be equal to each other.
Figure 4:
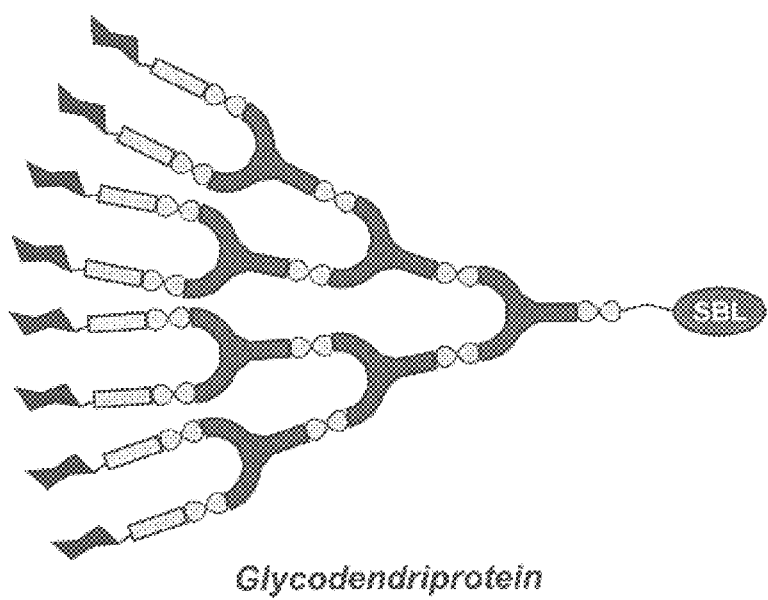
FIG. 4 is a schematic illustration of a glycodendriprotein showing terminal carbohydrate moieties, optional linkers, disulfide linkages, dendrimer cores, and a model enzyme, SBL.
Figure 10:
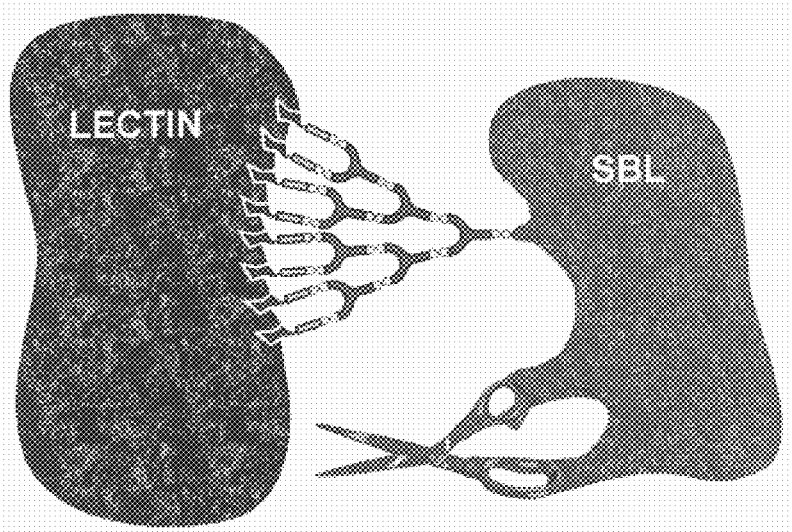
FIG. 10 illustrates the use of a glycodendriprotein to digest a lectin.
Figure 11:
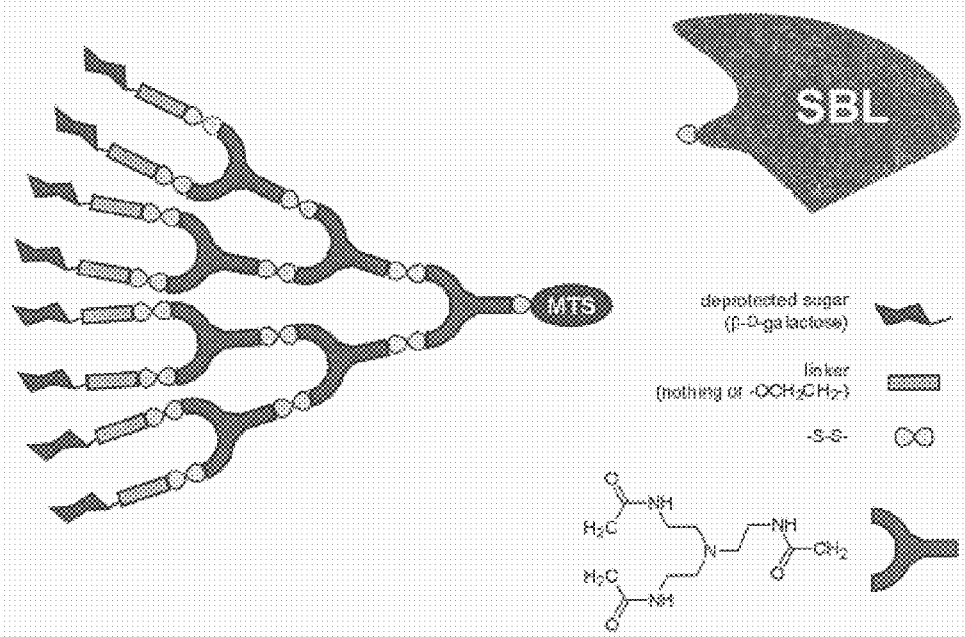
FIG. 11 illustrates components of a glycodendriprotein. The Y shaped dendrimer core illustrated is Type A (TREN-type), but also may represent Type B (Penta-E type), Type C (ArGal-Type) or other dendrimer core structures.

Lectins are sugar binding proteins. The sugar binding sites are relatively shallow and hence binding is comparatively weak. Lectins however often bind many saccharides of an oligosaccharide to give a strong, selective affinity between the lectin and a particular combination of saccharides. This is illustrated in FIG. 3. Briefly, the aim is to attach many sugars to the surface of a dendrimeric structure that is in turn attached to a protein to mimic the natural system. The model protein we used is subtilisin *Bacillus lentus* (SBL), a serine protease enzyme. If the glycodendrimer system synthesized has a strong affinity to the lectin being targeted, then the attached SBL (being a protease) should start 'cutting' up the lectin. This is shown schematically in FIG. 10. The specific model glycodendrimer that is the initial synthetic target of this project is shown in FIG. 11. SBL has no natural cysteines (and hence no thiols present). One can be introduced by way of site-directed mutagenesis. Methane thiosulfonate (MTS) reagents react specifically and quantitatively with thiols (Wynn, R.; Richards, F. M. *Methods Enzymol.* 1995, 201, 351) giving an excellent method for the attachment of the glycodendrimer to the protein.

Normal Addition

The following first-generation Type A glycodendrimer reagents were prepared according to the methods described in Davis, B. G., "The controlled glycosylation of a protein with a bivalent glycan: towards a new class of glycoconjugates, glycodendriproteins," *Chem. Commun.*, 2001, 351–352, the entire disclosure of which is incorporated by reference. FIG. 12, Scheme 6.

Two different representative bivalent branched glycan MTS reagents, 7'a and 7'b, based on a trivalent tris(2-aminoethyl)amine (TREN) core were synthesized (FIG. 12, Scheme 6). 7'a bears at the end of its two glycan branches the same untethered peracetylglucose unit that had previously allowed dramatic enhancement of enzyme activity. Lloyd, R. C., Davis, B. G., and Jones, J. B., *Bioorg. Med. Chem.*, 2000, 8, 1537. 7'b bears ethyl-tethered mannose moieties that had been used in the construction of previous glycoproteins that had shown low levels of lectin binding. Davis, B. G., Hodgson, D., Ullman, A., K. Khumtaveepom, Sala, R., Bott, R. R., and Jones, J. B. unpublished work. Lectin binding led to enhanced selectivity in the degradation of a mannose specific lectin by subtilisin *Bacillus lentus* ("SBL") glycosylated with a single mannose residue. These two reagents therefore allow the introduction of multivalent, tethered or untethered, glycans with α or β anomeric stereochemistry from different parent carbohydrate systems.

After differentiation of one of the two amine termini of TREN 1 through selective protection as its mono-Boc derivative (Tecilla, P., Tonellato, U., Veronese, A., Felluga, F., and Scrimin, P., *J. Org. Chem.*, 1997, 72, 7261), the two remaining free amine termini were reacted with chloroacetic anhydride to give the corresponding bis-α-chloroamide. Treatment of this branched dichloride with the potassium salt of thioacetic acid gave the bis-thioester 2 in a good overall yield (58% over 3 steps from 1). One-pot selective deprotection and glycosylations of 2 were achieved by treatment with dilute aqueous NaOH solution to hydrolyze the labile thioacetates and then appropriate modification of the free thiol groups produced with the appropriate untethered β-gluco 3a or tethered α-manno 3b methanethiosulfonate reagents to yield the corresponding bivalent branched glycans 6'a or 6'b in 73% and 62% yield, respectively. It should be noted that the use of a basic TREN-core as a scaffold allowed the scavenging of 6'a, b from reaction mixtures using acidic ion exchange resin and therefore greatly simplified their purification. With the ability to introduce two distinct glycan endgroups a or b thus suitably demonstrated, 7'a was deprotected through treatment with $CF_3COOH$ and the free amine produced converted to the corresponding α-chloroamide. Displacement of the α-chloro group through treatment with $NaSSO_2CH_3$ in DMF at 50° C. proceeded smoothly and yielded the target bis-glycan MTS 7'a in good yield (52% over 3 steps from 6'a).

Modified syntheses of a first-generation and a second generation (and in a similar manner, multi-generation) glycodendrimers and their subsequent attachments to thiol-containing amino acid side-chains to form the corresponding glycodendriproteins are outlined in Scheme 7 (FIG. 13) and Scheme 8 (FIG. 14), respectively.

Results and Discussion

Figure 13:
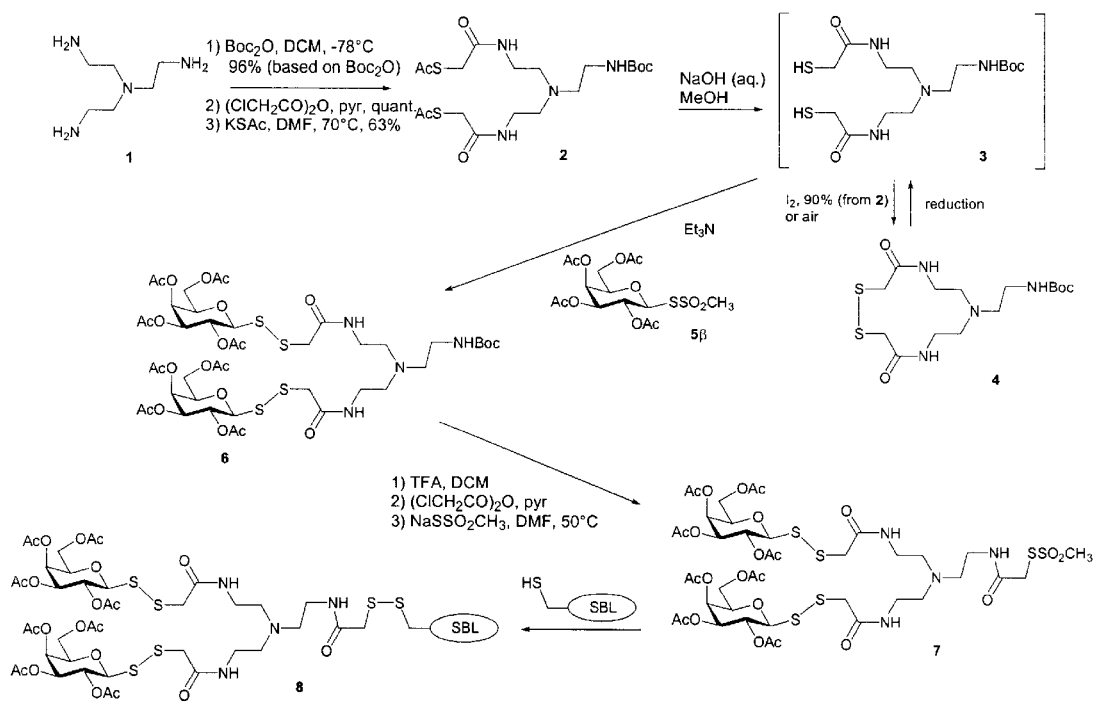
FIG. 13 shows a normal addition synthetic scheme for producing a glycodendriprotein.

The initial dendrimeric core building block was prepared from tris(2-aminoethyl)amine (TREN) 1 using literature methodology (Tecilla, P.; Tonellato, U.; Veronese, A. *J. Org. Chem.* 1997, 62, 7621) and that described in Scheme 7 (FIG. 13). Excess 1 is reacted with $Boc_2O$ to selectively give the mono-Boc protected TREN. After chromatographic purification, the remaining amines were protected with chloroacetates and the chlorines displaced with thioacetates to give 2. The acetates were deprotected under mild basic conditions to give the dithiol 3. It had previously been noted that this product is slowly oxidized to the disulfide 4 on exposure to air making purification and subsequent use of 3 problematic. The dithiol was therefore deliberately oxidized directly to 4 by the addition of iodine. This gave a product that was much more amenable to storage and purification by chromatography.

The next step is the attachment of the sugars to the dendrimeric core. Because of the stability problems of the dithiol 3, many attempts were made to generate it in situ. This type of coupling is one of the most important reactions in building of multi-generation glycodendriproteins (Scheme 8) and hence an elegant, high yielding reaction would be very useful. These attempts to generate the dithiol 3 in situ took two forms, either (a) reducing the disulfide 4 or (b) deprotecting the diacetate 2.

The problems associated with the former method are that only one equivalent of reducing reagent must be used to stop unwanted reduction of the product. In addition, the presence of the oxidized reductant may disrupt the coupling reaction. Ideally the latter method would utilize a base that was basic enough to deprotect the S-acetates but not basic enough to cleave the O-acetates.

In both cases, care must be taken to avoid the oxidation of the dithiol 3 before it can couple with the MTS reagent. This includes 'degassing' the solvents to reduce the amount of oxygen present.

Reduction of Disulfide 4

Figure 15:
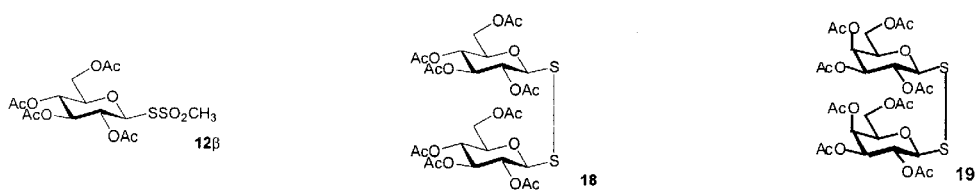
FIG. 15 shows glyco MTS reagent 12β, and diglycosyl disulfides 18 and 19 resulting from the use of 12β or 5β the in situ reduction approach described in Example 2.
Figure 15:
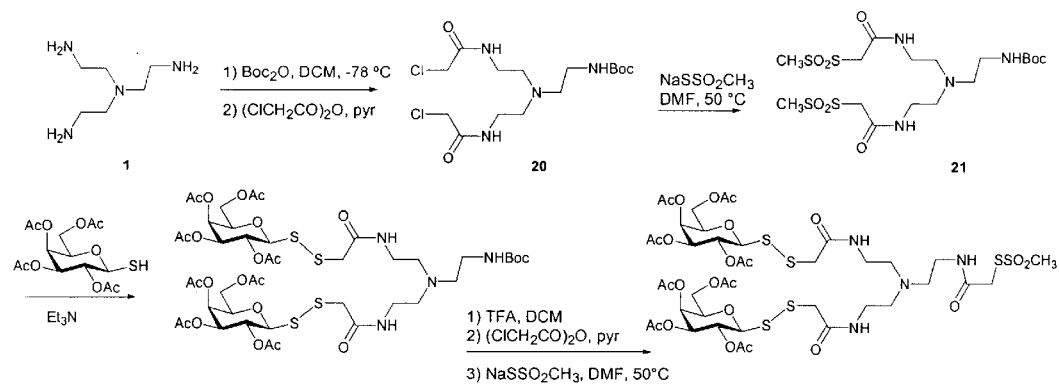

Two methods were used to prepare dithiol 3 in situ by reduction. Disulfide 4 was treated with one equivalent of the 'organic' reductant, tributyl phosphine, and the resulting solution added dropwise to the MTS reagent in the presence of mild base. No coupling was observed by TLC and no coupled product isolated by chromatography. Some of the diglycosyl disulfide 18 or 19 (c.f. β-Gal-SS-β-Gal in: Kiefel, M. J.; Thomson, R. J.; Radovanovic, M.; von Itzstein, M. *J. Carbohydr. Chem.* 1999, 18, 937) (depending on the MTS reagent used, 12β or 5β) was isolated (FIG. 15). This implies that thiols had been present in the reaction. Attempts with the 'inorganic' reductant, sodium metabisulfite, were also unsuccessful.

Deprotection of Diacetate 2

The first attempt using this approach involved reacting the diacetate 2 directly with MTS reagent 5β in the presence of excess triethylamine. Triethylamine is required for the coupling of the dithiol 3 with MTS reagent 5β anyway, and the hypothesis was this base could also deacetylate 2 to give the dithiol 3 in situ. Precedent for this is given in: Greene. T. W., Wuts, P. G. M. *Protective Groups in Organic Synthesis,* 2nd ed. John Wiley & Sons Inc., 1991, New York. This was however unsuccessful. This reaction was repeated but using the stronger base, diisopropylethylamine which had been shown previously (by TLC) to deacetylate 2. Again, no coupling product was observed.

The next step was to then try more conventional deacetylation reagents. Most deacetylations involve the use of catalytic amounts of the methoxide anion in methanol. Deprotection of ROAc with $MeO^-$ gives $RO^-$ and AcOMe. The solvent then protonates the deprotected alkoxide to give ROH and regenerates the catalyst $MeO^-$. However in the deprotection of alkyl thioacetates, thiols are more acidic than alcohols and so the equilibrium lies in favor of $RS^-$ rather than $MeO^-$. Hence, for deprotection to go to completion, an excess of alkoxide per thioacetate is required. To avoid deprotection (for ease of purification) of the resulting coupled product, any excess base ideally should be neutralized before coupling.

One source of methoxide is the use of anhydrous methanol saturated with anhydrous ammonia. This has the advantage that after deprotection of the diacetate 2, excess base can just be removed by concentration of the solution in vacuo. Several attempts were made to couple 12β with dithiol 3 generated in this way (i.e., according to Scheme 7), however no coupling product was observed. Eventually all the MTS reagent would end up as the disulfide 18 (FIG. 15). The stability of MTS reagents (in this case, 12β) to ammonia was examined. To a $CDCl_3/CD_3OD$ solution of 12β was added a drop of aqueous ammonia. $^1H$ NMR spectra of this sample before and after ammonia addition gave different spectra, suggestion the formation of an activated sugar-S—$NH_2$ type species. However concentrating the solution in vacuo gave back the MTS reagent 12β. Electrospray mass spectrometry was carried out on this solution which showed $[M+Na]^+$ for 12β, 18 and an unknown peak at m/z 436.

Many attempts to deprotect diacetate 2 with other basic conditions (for example, aqueous NaOH in methanol or sodium methoxide in methanol) followed by reaction with an MTS reagent (either directly or after neutralization, or after neutralization and isolation of dithiol 3) failed to give high coupling yields. For example, 10% coupling was observed from deprotection with 1.1 equivalents of sodium methoxide in methanol and then direct reaction with a MTS reagent.

The difficulty observed with this coupling could in part be due to the facile nature of the intramolecular disulfide formation of disulfide 4 (FIG. 13, Scheme 7). The above results lead to the suggestion that the coupling could be carried out in the reverse direction, i.e., with the MTS reagent on the dendrimer core and the free thiol on the sugar. See Inverse Addition section below and Scheme 9, FIG. 15. The oxidative side reaction of the thiols to give a disulfide would now be an intermolecular process and known to not be competitive with the MTS coupling reaction. The inverse addition strategy proved to be efficient and actually requires fewer synthetic steps than the normal addition coupling described in Schemes 6, 7 and 8, above.

Inverse Addition

Figure 16:
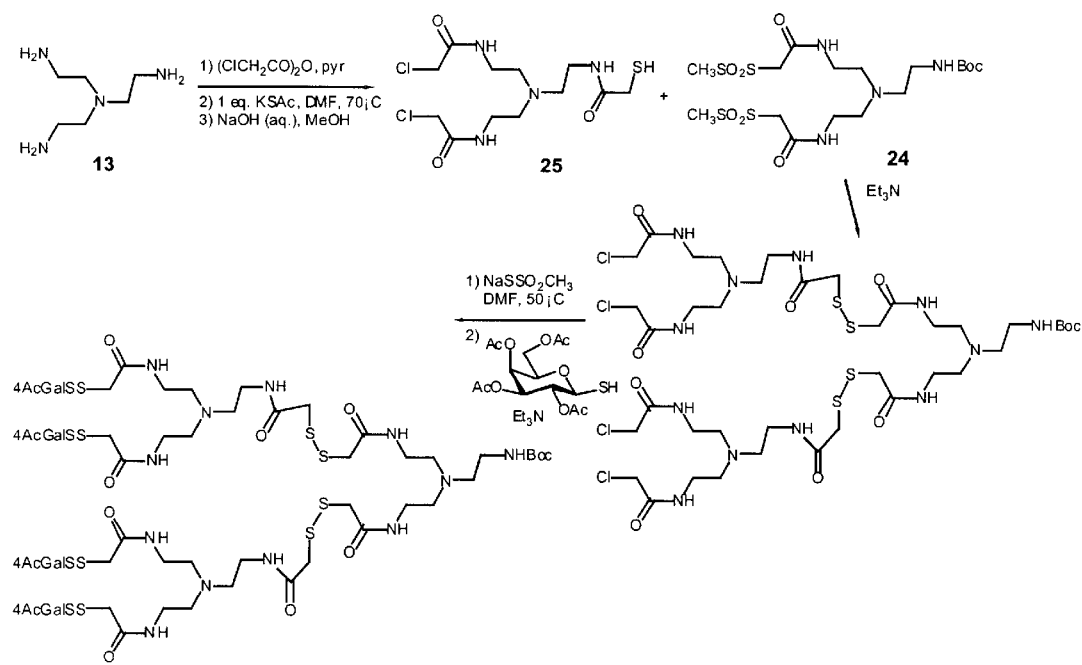
FIG. 16 shows an inverse addition synthesis scheme for a multi-generation glycodendrimer reagent.

This new inverse-addition approach for the synthesis of first- and multi-generation glycodendriproteins is outlined in Scheme 9 (FIG. 15) and Scheme 10 (FIG. 16). It is based on the realization that improved coupling efficiency between the carbohydrate moiety and the dendrimer core is obtained by adding the methanethiosulfonate moiety to the ends of the dendrimer core, and reacting the dendrimer core with a sulfhydryl-bearing carbohydrate moiety.

The dichloroacetyl 20 was prepared as outlined in Scheme 9. Initially, we attempted synthesis of 21 through the reaction of 20 with sodium methanethiosulfonate. (Scheme 9) This approach, however, did not give an appreciable yield of bis-MTS reagent 21. The similar reaction involving 31 (Scheme 11, FIG. 17) was also problematic. Substitution of a chloride α to a carbonyl does not appear to be as facile as for other alkyl halides. This has lead to the investigation of inserting a longer alkyl chain between the halide and the amide (discussed later).

Figure 17:
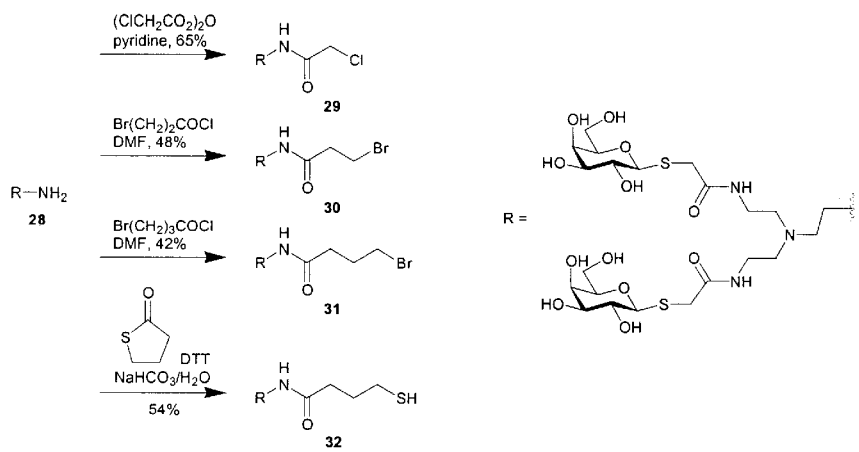
FIG. 17 shows Scheme 11, illustrating synthetic approaches for producing bis-MTS reagents; Scheme 12, for producing thioglycoses; and Scheme 13, illustrating another synthetic method for generating a first generation glycodendrimer reagent.
Figure 17:
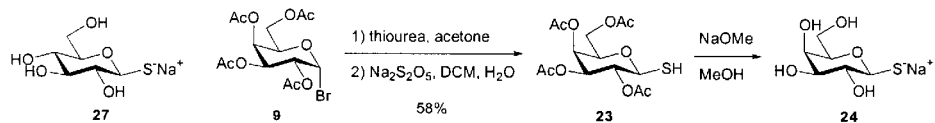
Figure 17:
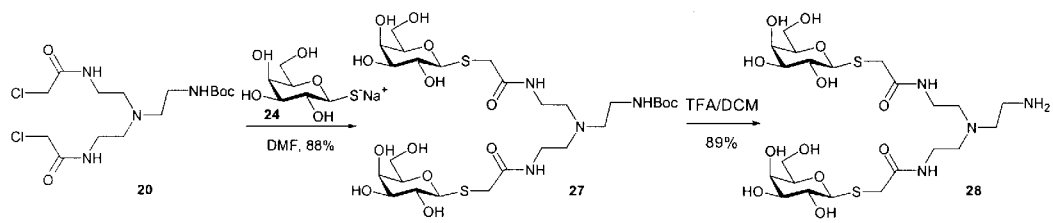

Thioglycoses 23, 24 and 27 (see Scheme 12, FIG. 17) all are available commercially or may be readily prepared. For example 24 was prepared as described in Scheme 12 (FIG. 17). Another direct method to a first generation glycodendrimer can be seen in Scheme 13 (FIG. 17). The deprotected sodium salt of 1-thiogalactose 24 readily reacts with the bis-halide 20 to give the bis-galactoside 27 which can then be deprotected to give the amine 28. Purification of these comparatively high polarity compounds allowed the synthesis of 28 in good overall yields. The amine 28 was chloroacetylated to give 29 (Scheme 11, FIG. 17). However, as mentioned above, subsequent reaction with sodium methanethiosulfonate to give a glycodendrimer MTS reagent did not result in appreciable yields of the expected product. It was thought that increasing the distance between the halide and amide should solve this problem. Precedent for this is supplied by preparation of MTS reagent 3 in excellent yield from bromide 2 (Scheme 1, FIG. 6).

The reaction of 3-bromopropionoyl chloride with amine 28 on a NMR scale gave the required product 30 (Scheme 11, FIG. 17). This acylating reagent (i.e., 3-bromopropionoyl chloride) was also reacted with TREN 1 (Scheme 14, FIG. 8) with the aim of preparing the tris-MTS reagent 34 (n=2). Initial attempts to acylate TREN 1 with 3-bromopropionoyl chloride were done in the presence of base. This however led to elimination products being observed. Elimination of HBr is favorable due to the production of a conjugated α,β-unsaturated system. Repeating this acylation in DMF without any base present gives the required product 33 (n=2). The identity of this product was confirmed by spectroscopic methods and by reacting with sodium methanethiosulfonate to give 34 (n=2).

To avoid the problem of HBr elimination, the homologue acylating reagent (4-bromobutyryl chloride) has also been investigated. Acylation of amine 28 gave 31 (Scheme 11, FIG. 17), however subsequent reaction with sodium methanethiosulfonate only gave baseline material by TLC (10% saturated aqueous ammonia in methanol). TLC of the starting material ($R_f$=0.3 in this solvent system) showed that it had since decomposed to baseline material.

Figure 18:
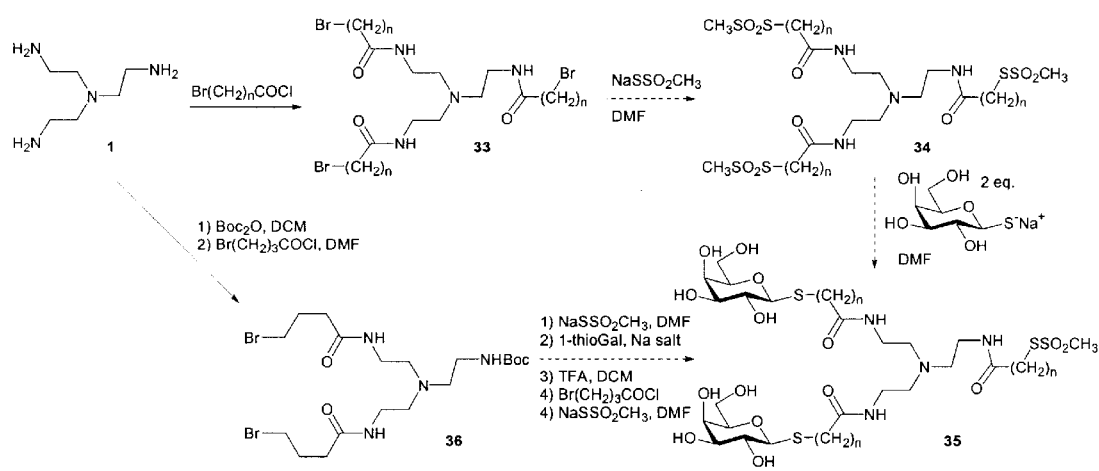
FIG. 18 shows another synthetic scheme for producing a glycodendrimer MTS reagent.

Preparation of 36 (Scheme 14, FIG. 18) involved acylation of TREN-Boc with excess reagent 4-bromobutyryl chloride. Addition of base (triethylamine) was required to get the reaction to go to completion. It is assumed that the HCl produced was giving the hydrochloride salt of the unreacted amines, halting reaction. The major product appeared to be 33 (n=3), suggesting that the acid production had cause deprotection of the Boc group. Subsequent reaction with sodium methanethiosulfonate however gave a product of the form $XCO(CH_2)_3SSO_2CH_3$ (that is, no TREN component observed), refuting this notion.

Figure 19:
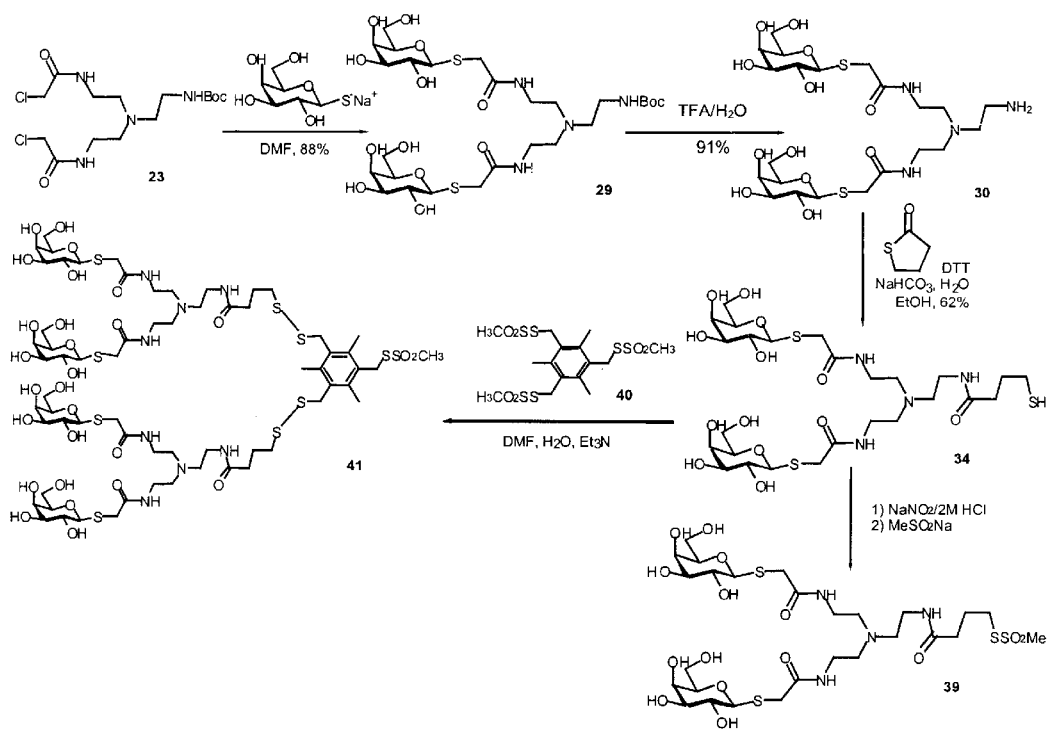
FIG. 19 shows a synthetic scheme (Scheme 15) for producing a first generation glycodendrimer MTS reagent, and a second generation hybrid glycodendrimer MTS reagent; and an improved synthesis scheme (Scheme 16) for producing sodium methanethiosulfonate ("NaMTS").
Figure 19:
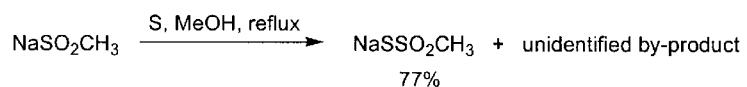

As stated above, a terminal amine functionality on the dendrimer core was converted to a terminal thiol by chloroacetylation, substitution with thioacetate and then deacetylation. An alternative method for this terminal conversion is described by Blixt and Norberg. Blixt, O.; Norberg, T. *J. Org. Chem.* 1998, 63, 2705–2710. These authors report reacting 2-aminoethyl 2-acetamide-2-deoxy-β-D-glucopyranoside with γ-thiobutyrolactone in the presence of aqueous base and DTT (to stop disulfide formation) to give the corresponding ring-opened thiol in 71% yield. Amine 30 (Scheme 15, FIG. 19) was treated in the same way to give the expected thiol 34 in moderate yield. This is a useful product for the preparation of second-generation glycodendrimers (by reaction with bis-MTS reagents of type 21). 34 was then used in the synthesis of the di-Gal-TREN-MTS 39 via a nitrosylation reaction and reaction with methanesulfinate (Scheme 15, FIG. 19). 34 was also used to synthesize the tetra-Gal-TREN/araGal hybrid-MTS 41 (Scheme 15, FIG. 19).

Experimental

TREN-Boc Disulfide 4

TREN-SAc 2 (100 mg, 0.209 mmol) was dissolved in methanol (4.5 mL) and 2 M aqueous NaOH (0.5 mL). After 20 minutes deprotection was complete (assayed by TLC) and so the mixture was neutralized with acetic acid oxidized with iodine (60 mg, 0.236 mmol). After 1 hour, the mixture was concentrated in vacuo and purified using flash silica column chromatography and eluted with 10% methanol in ethyl acetate to give 4 in 90% yield. $^1$H NMR (300 MHz, CD$_3$OD) δ 1.44 (s, 9H, (CH$_3$)$_3$), 2.68–2.76 (m, 6H, CH$_2$N (CH$_2$)$_2$), 3.22 (t, J 6.1 Hz, 2H, CH$_2$NHBoc), 3.29–3.35 (m, 4H, CH$_2$NHCOCH$_2$SS), 3.61 (s, 4H, CH$_2$SS).

Bis{N-[2-(1-thio-β-D-galactopyranosyl)ethanoyl] aminoethyl}-{N-tert-butylcarbamoylaminoethy}amine 27

1-Thio-β-D-galactopyranose, sodium salt (417 mg, 1.91 mmol) was added to bis[N-(2-chloroethanoyl)aminoethyl]-[N-tert-butylcarbamoylaminoethyl]amine 20 (332 mg, 0.83 mmol) in DMF (15 mL). The suspension was stirred at room temperature. After three hours, the thiosugar had dissolved and a fine white precipitate had formed. The mixture was concentrated in vacuo and the residue purified by flash silica column chromatography, eluting with chloroform/methanol/sat. aq. ammonia (60:30:8) to give the title compound as a colorless foam (528 mg, 88%); $[α]_{22}^D$=−26.6 (c 1.0, H$_2$O); $^1$H NMR (500 MHz, D$_2$O) δ 1.28 (s, 9H, Boc), 2.74 (br s, 6H, N(CH$_2$CH$_2$)$_3$), 3.09 (br s, 2H, NCH$_2$CH$_2$NHBoc), 3.26 (br s, 4H, NCH$_2$CH$_2$NHCO), 3.27 (d, J 15.3 Hz, 2H, COCHH'S), 3.40 (d, J 15.3 Hz, 2H, COCHH'S), 3.43 (dd, J 9.6, 9.4 Hz, 2H, H2'), 3.49 (dd, J 9.4, 3.2 Hz, 2H, H3'), 3.53–3.59 (m, 6H, H5', H6'), 3.82 (d, J 2.9 Hz, 2 H, H4'), 4.33 (d, J 9.6 Hz, 2H, H1'); $^{13}$C NMR (125 MHz, D$_2$O) δ 27.8 (NHBoc), 33.3 (SCH$_2$CO), 36.9 (N(CH$_2$CH$_2$)$_3$), 52.6 (NCH$_2$CH$_2$NHBoc), 53.0 (NCH$_2$CH$_2$NHCOCH$_2$), 61.2 (C6'), 68.9 (C4'), 69.6 (C2'), 73.9 (C3'), 79.2 (C5'), 81.4 (Boc), 85.7 (C1'), 158.3 (NHCOO), 173.0 (NHCOCH$_2$S).

2-(Bis{N-[2-(1-thio-β-D-galactopyranosyl)ethanoyl]aminoethyl}amino)ethylamine 30

Bis {N-[2-(1-thio-β-D-galactopyranosyl)ethanoyl]aminoethyl}-{N-tert-butylcarbamoylaminoethyl}amine 29 (1.35 g, 1.88 mmol) was stirred in trifluoroacetic acid (12 mL) and water (12 mL). After one hour, the solution was concentrated in vacuo and the residue loaded on to a Dowex 50W2-200 (H$^+$) column in water/methanol (1:1). The column was washed with 80 mL volumes of methanol, water/methanol (1:1) and water and then the product removed by eluting with 15% aqueous ammonia to give the title compound as a colorless foam (1.06 g, 91%); [α]$_{22}^{D}$=−28.0 (c 1.0, H$_2$O); $^1$H NMR (500 MHz, D$_2$O) δ (COCH$_2$S peaks not seen due to deuterium exchange) 2.48 (t, J 6.7 Hz, 2H, NCH$_2$CH$_2$NH$_2$), 2.53 (t, J 6.7 Hz, 4H, NCH$_2$CH$_2$NHCOCH$_2$S), 2.61 (t, J 6.7 Hz, 2H, NCH$_2$CH$_2$NH$_2$), 3.17 (t, J 6.7 Hz, 4H, NCH$_2$CH$_2$NHCOCH$_2$S), 3.41 (dd, J 9.7, 9.4 Hz, H2 '), 3.48 (dd, J 9.4, 3.3 Hz, H3'), 3.51–3.59 (m, 6H, H5', H6 '),3.19 (d, J 3.2 Hz, 2H, H4'), 4.32 (d, J 9.7 Hz, 2H, H1'); $^{13}$C NMR (125 MHz, D$_2$O) δ 32.8 (COCH$_2$S), 37.4 (NCH$_2$CH$_2$NH), 37.8 (NCH$_2$CH$_2$NH$_2$), 52.3 (NCH$_2$CH$_2$NH), 54.6 (NCH$_2$CH$_2$NH$_2$), 61.2 (C6 '), 68.9 (C4'), 69.6 (C2'), 73.9 (C3'), 79.2 (C5'), 85.6 (C1 '), 172.7 (NHCOCH$_2$S); HRMS m/z (ES): found 619.2320; C$_{22}$H$_{43}$N$_4$O$_{12}$S$_2$[M+H] requires 619.2319.

N-[2-(Bis{N-[2-(1-thio-β-D-galactopyranosyl)ethanoyl]aminoethyl}amino)ethyl]-4-mercaptobutyramide 34

2-(Bis {N-[2-(1-thio-β-D-galactopyranosyl)ethanoyl]aminoethyl }amino) ethylamine 30 (241 mg, 0.39 mmol) was dissolved in a NaHCO$_3$ aqueous solution (0.5 molL$^{-1}$, 10 mL) and ethanol (3 mL). Dithiothreitol (300 mg, 1.95 mmol) and γ-thiobutyrolactone (337 μL, 3.90 mmol) were added and the mixture heated under nitrogen overnight at 50° C. The resulting mixture was neutralized with HCl (2 molL$^{-1}$) and concentrated in vacuo. The residue was purified by flash silica column chromatography, eluting with chloroform/methanol/water/triethylamine (60:35:7:1), to give the product contaminated with triethylammonium chloride. This was loaded on to a Dowex 50W2-200 (H$^+$) column in water, washed with water and then the product removed by eluting with 10% aqueous ammonia to give title compound (174 mg, 62%) as a colorless foam; [α]$_D^{16}$=−27.8 (c 0.6, H$_2$O); $^1$H NMR (500 MHz, D$_2$O) δ 1.74 (tt, J 7.1, 7.3 Hz, 2H, CH$_2$CH$_2$SH), 2.24 (t, J 7.3 Hz, 2H, CH$_2$(CH$_2$)$_2$SH), 2.41 (t, J 7.1 Hz, 2H, CH$_2$SH), 2.56–2.62 (m, 6H, NCH$_2$), 3.17 (t, J 6.5 Hz, 2H, NCH$_2$CH$_2$NHCO(CH$_2$)$_3$SH), 3.20 (t, J 6.7 Hz, 2H, NCH$_2$CH$_2$NHCOCH$_2$S), 3.28 (d, J 15.4 Hz, 2H, COCHH'S), 3.41 (d, J. 15.4 Hz, 2H, COCHH'S), 3.45 (dd, J 9.6, 9.4 Hz, 2H, H2'), 3.51 (dd, J 9.4, 3.1 Hz, H3 '), 3.54–3.63 (m, 6H, H5', H6'), 3.84 (d, J 3.1 Hz, 2H, H4'), 4.35 (d, J 9.6 Hz, 2H, H1'); $^{13}$C NMR (125 MHz, D$_2$O) δ 23.3 (CH$_2$SH), 29.6 (CH$_2$CH$_2$SH), 33.3 (NHCOCH$_2$S), 34.6 (CH$_2$CH$_2$CH$_2$SH), 37.0 (CH$_2$NHCO(CH$_2$)$_3$SH), 37.4 (SCH$_2$CONHCH$_2$), 52.2 (NCH$_2$CH$_2$NHCOCH$_2$S), 52.3 (NCH$_2$CH$_2$NHCO(CH$_2$)$_3$SH), 61.2 (C6'), 68.9 (C4'), 69.6 (C2'), 74.0 (C3'), 79.2 (C5'), 85.6 (C1'), 172.6 (NHCOCH$_2$S), 176.2 (NHCO(CH$_2$)$_3$SH); HRMS m/z (ES): found 721.2459; C$_{26}$H$_{49}$N$_4$O$_{13}$S$_3$[M+H] requires 721.2458.

Second-Generation Galactodendrimer MTS Reagent tetra-Gal-TREN/AraGalhybrid-MTS 41:

Tris(methanethiosulfonatomethyl)mesitylene 40 (26 mg, 0.05 mmol) and triethylamine (15 μL, 0.10 mmol) were dissolved in DMF (20 mL) in an ice/salt bath. A solution of N-[2-(Bis {N-[2-(1-thio-β-D-galactopyranosyl)ethanoyl]aminoethyl}amino)ethyl]-4-mercaptobutyramide 34 (75 mg, 0.10 mmol) in water (20 mL) was added dropwise over 2 hours. The resulting solution was allowed to warm to room temperature, left over night and then concentrated in vacuo. ESMS of the residue gives a spectrum consistent with the presence of the title compound.

Methanethiosulfonic Acid S-{3-[2-N-[2-(Bis{N-[2-(1-thio-β-D-galactopyranosyl)ethanoyl]aminoethyl}amino)ethylcarbamoyl]propyl}ester 39

N-[2-(Bis {N-[2-(1-thio-β-D-galactopyranosyl)ethanoyl]aminoethyl}amino)ethyl]-4-mercaptobutyramide 34 (108 mg, 0.15 mmol) was dissolved in 2 M HCl (4 mL) and cooled to 0° C. Sodium nitrite (10 mg, 0.15 mmol) in water (1 mL) was added. After the addition, the now red solution was left at 0° C. for 15 mins and then at 4° C. for a further 90 mins. Methanesulfinic acid, sodium salt (31 mg, 0.30 mmol) in a water (2 mL) was added and the solution left at room temperature for 4 hours by which stage most of the red color had gone. The solution was carefully neutralized with aqueous NaOH and concentrated in vacuo. ESMS of the residue gives a spectrum consistent with the presence of the title compound.

Example 3

ArGal-based (Type B) Glycodendrimer Synthesis Improved Synthesis for NaMTS

An alternative preparation of NaMTS (J. D. Macke, L. Field, *J. Org. Chem.* 1988, 53, 396–402) has been successfully tested, which is faster and avoids the tedious and lengthy separation of by-product from NaMTS as required in the Na$_2$S/Me$_3$SiCl method. NaMTS was synthesized in high yield by refluxing sodium sulfinate with sulphur in methanol (Scheme 16, FIG. 19), described in further detail below). Although formation of small amounts of an unknown by-product was observed, it could be easily separated from NaMTS.

Inverse Addition Synthesis of Type B Glycodendrimer Reagent

Figure 20:
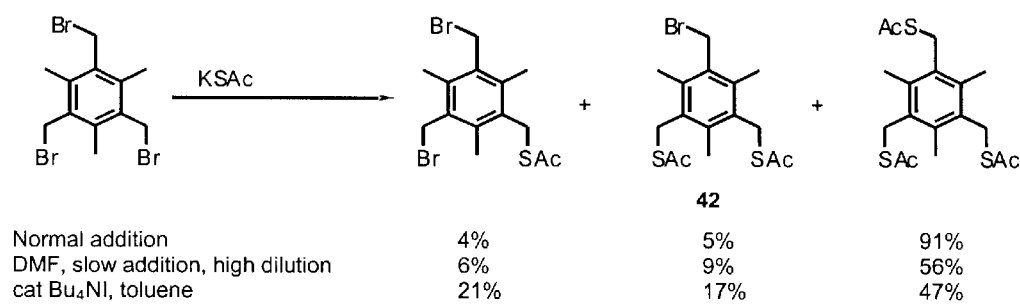
FIG. 20 shows synthetic scheme 17 for producing ArGal-based (Type B) glycodendrimer reagent 42; and synthetic scheme 18 for producing ArGal-based (Type B) glycodendrimer reagent 44, bearing two deprotected sugars.
Figure 20:
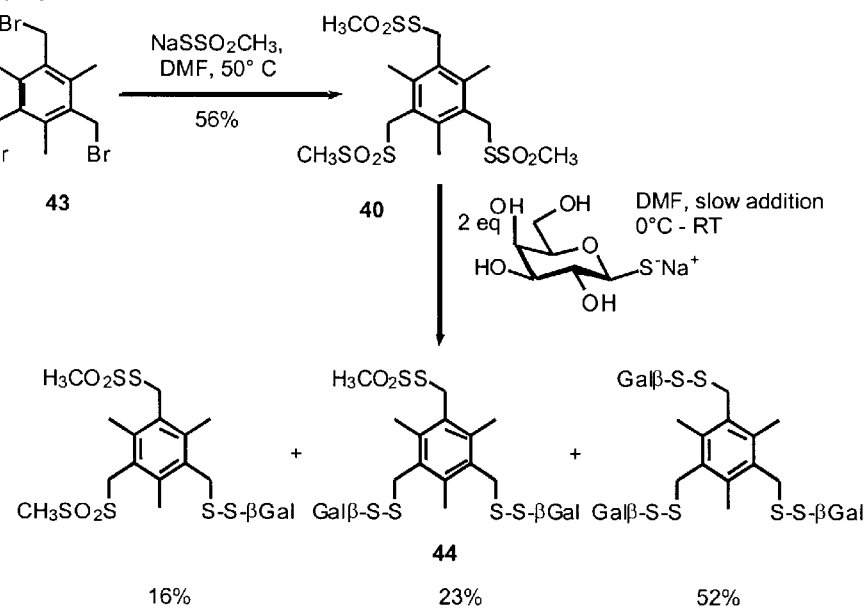
Figure 21:
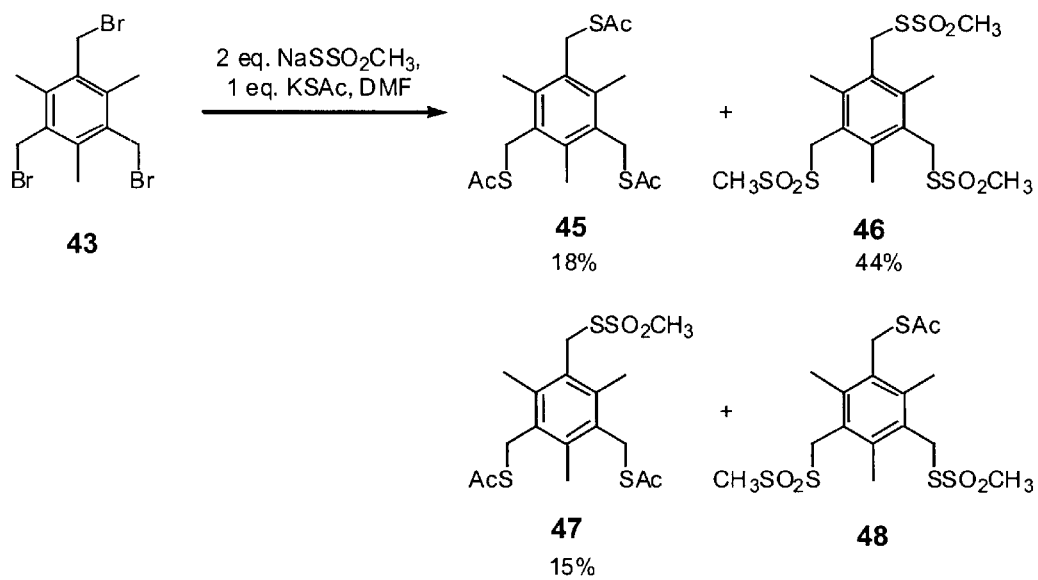
FIG. 21 illustrates synthetic scheme 19 and synthetic scheme 20 for producing Type B glycodendrimer reagents.
Figure 21:
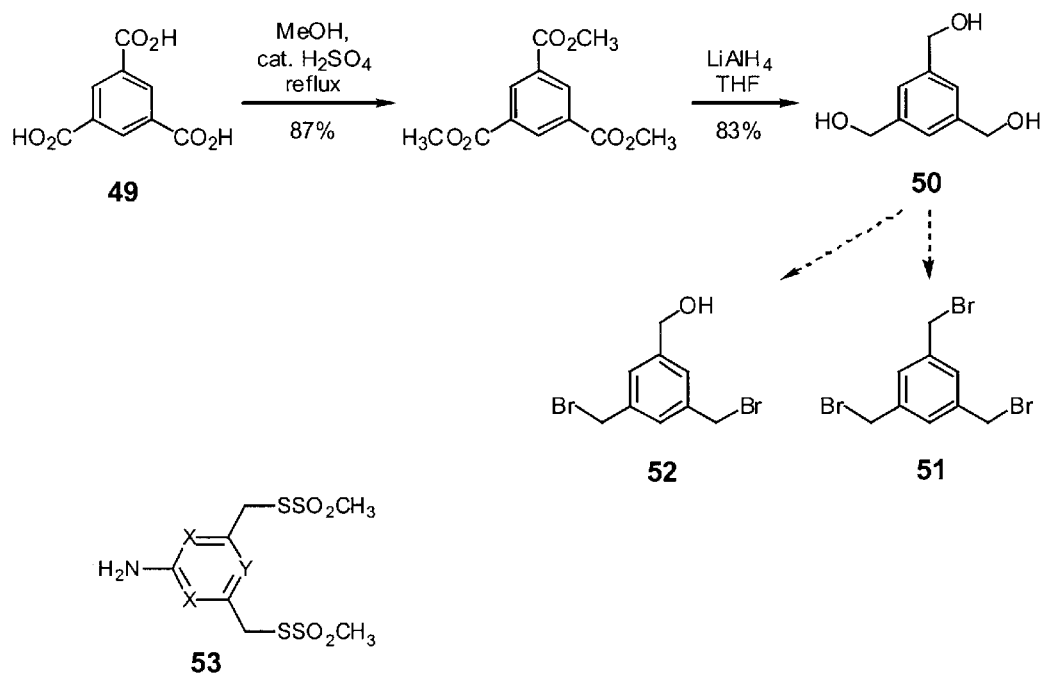

Two synthetic approaches for building block 42 were undertaken (Scheme 17, FIG. 20). Slow addition of KSAc under high dilution resulted in a 9% yield of 42. Better results were obtained under phase transfer conditions with catalytic amounts of Bu$_4$NI as phase transfer catalyst and toluene as solvent. In this case 42 was isolated in 17% yield.

A short synthesis of MTS reagents with two deprotected sugars on has been developed (Scheme 18, FIG. 20). The bromide 43 was reacted with NaMTS to yield the methanethiosulfonate 40 in moderate yield, which was then treated with 2 equivalents of the sodium salt of 1-thio-β-D- galactose to afford the desired diGal-ArGal-MTS reagent 44 in 23% yield. As before, the main product was the trisubstituted compound.

Figure 22:
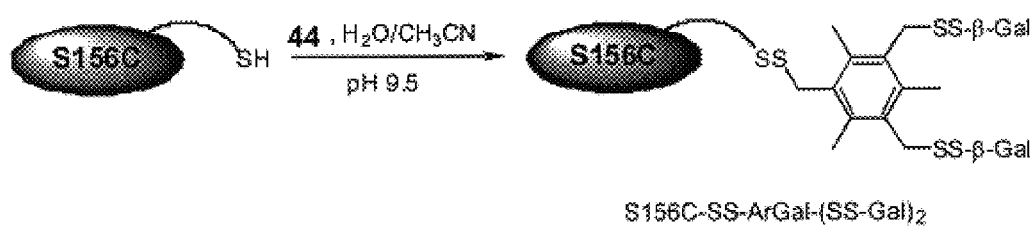
FIG. 22 illustrates synthetic scheme 21 for producing a Type B glycodendriprotein.
Figure 23:
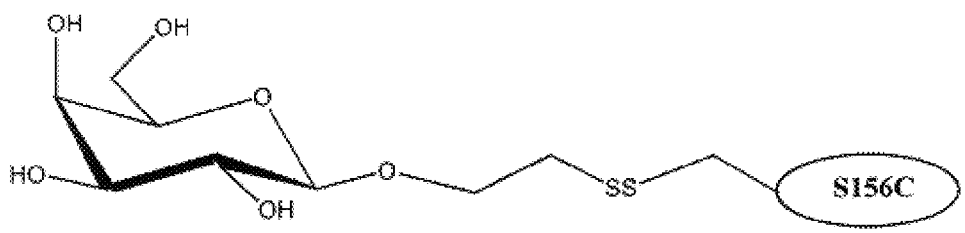
FIG. 23 illustrates a glycosylated variant of *Bacillus lentus* subtilisin mutant S156C.

Modification of Cysteine-Containing Protein with Type B Glycodendrimer Reagent A cysteine-containing mutant of subtilisin *Bacillus lentus*, S156C, was modified with the Type B glycodendrimer reagent glycoMTS 44 to give the glycodendriprotein S156C-Mes(SS-β-Gal)$_2$ ("di-gal protease")(Scheme 21, FIG. 22).

Experimental

Synthesis of Sodium methanethiosulfonate (NaMTS) (J. D. Macke, L. Field, J. Org. Chem. 1988, 53, 396–402)

A mixture of sodium methanesulfinate (5.43 g, 53 mmol) and sulphur (1.666 g, 52 mmol) in dry methanol (310 ml) was heated to reflux for 20 min, at which time almost all of the sulphur had dissolved. The hot solution was filtered and the filtrate concentrated to dryness. The off-white solid was stirred with a small amount of dry ethanol at room temperature, filtered and concentrated. The trituration was repeated until $^1$H NMR of the white residue showed no more traces of sodium methanethiosulfonate. The filtrates were then combined and evaporated to dryness to yield the title compound (5.40 g, 77%) as fine white needles; mp 271–272° C. (lit. [G. L. Kenyon, T. W. Bruice, *Methods Enzymol.* 1977, 47, 407–430.]272–273.5° C.); $^1$H NMR (200 MHz, CDCl$_3$) δ 3.18 (s, 3H, CH$_3$); anal. calculated. for CH$_3$NaO$_2$S$_2$: C 8.95, H 2.25; found: C 8.86, H 2.55.

Synthesis of 1,3-Bis(acetylsulfanylmethyl)-5-bromomethyl-2,4,6-trimethyl-benzene (42)

Synthesis A

DMF, Slow Addition, High Dilution

A solution of potassium thioacetate (0.354 g, 3 mmol) in dry DMF (35 ml) was added dropwise over a period of 6 h to a solution of mesitylene tribromide (0.612 g, 1.5 mmol) in dry DMF (45 ml). After the end of the addition, stirring was continued over night at room temperature. The reaction mixture was diluted with water (50 ml) and extracted with CH$_2$Cl$_2$ (4×50 ml). The combined organic phases were washed with brine, dried over MgSO$_4$, and the solvents removed. The remaining beige solid was separated by flash chromatography (SiO$_2$, hexane:EtOAc, gradient elution, 10:1 to 5:1) to afford 3 products: 1-acetylsulfanylmethyl-3,5-bis(bromomethyl)-2,4,6-trimethyl-benzene (0.032 g, 5%) as a white solid, 42 (0.051 g, 9%) as a white solid, and tris-(acetylsulfanylmethyl)-mesitylene (0.215 g, 56%) as a white solid; analytical data for mono-SAc: MS m/z (EI+) 396(7%), 394 (M$^+$, 12%), 392(6%), 315 (100%), 313 (97%), 239 (58%), 237 (59%), 191 (25%), 158 (43%); anal. calcd. for C$_{14}$H$_{13}$Br$_2$OS: C 42.66, H 4.60, Br 40.54, S 8.14; found: C 42.78, H 4.62, Br 40.59, S 8.14; analytical data for 42: MS m/z (EI+) 390 (M$^+$, 14%), 388 (M$^+$, 13%), 309 (100%), 233 (40%), 191 (20%), 157 (34%); analytical data for tris-SAc: MS m/z (EI+) 384 (M$^+$, 31%), 309 (M$^+$-SAc, 100%), 233 (58%), 157 (55%); anal. calcd. for C$_{18}$H$_{24}$O$_3$S$_3$: C 56.22, H 6.31, S 25.05; found: C 56.00, H 6.31, S 25.05.

Synthesis B

Bu$_4$NI, Toluene

A mixture of mesitylene tribromide (0.613 g, 1.5 mmol), Bu$_4$NI (0.055 g, 0.15 mmol) and potassium thioacetate (0.354 g, 3 mmol) in toluene (20 ml) was stirred for 4.5 h at room temperature. The reaction mixture was diluted with toluene (25 ml), washed with water (2×25 ml) and brine, dried over MgSO$_4$, and the solvent removed. The remaining residue was a purified by flash chromatography (SiO$_2$, hexane: EtOAc, 10:1) to yield mono-SAc (0.114 g, 21%) as a white solid, 42 (0.092 g, 17%) as a white solid, and iris-SAc; (0.184 g, 47%) as a white solid.

Synthesis of Tris-(methanthiosulfonatomethyl)-mesitylene (40)

Sodium methanethiosulfonate (0.429 g, 3.15 mmol) and the bromide 43 (0.400 g, 1 mmol) were dissolved in dry DMF (20 ml) and stirred at 50° C. under N$_2$ over night. The reaction mixture was cooled to room temperature, diluted with water and extracted with CH$_2$Cl$_2$ (4×25 ml) and EtOAc (4×25 ml). The combined organic extracts were concentrated in vacuo and the crude product was chromatographed (SiO$_2$, EtOAc: hexane, 2:1) to give 40 (0.277 g, 56%) as an off-white solid; $^1$H NMR (300 MHz, CDCl$_3$) δ 2.44 (s, 3H, CH$_3$), 3.32 (s, 3H, SO$_2$CH$_3$), 4.43 (s, 2H, CH$_2$); $^{13}$C NMR (75 MHz, CDCl$_3$) δ 16.4 (CH$_3$), 36.3 (CH$_2$), 50.2 (SO$_2$CH$_3$), 129.1 (aromat. C-2), 138.3 (aromat. C-1); $^1$H NMR (200 MHz, acetone-d6) δ 2.55 (s, 3H, CH$_3$), 3.55 (s, 3H, SO$_2$CH$_3$), 4.64 (s, 2H, CH$_2$); $^{13}$C NMR (50 MHz, acetone-d6) δ 15.8 (CH$_3$), 36.3 (CH$_2$), 49.7 (SO$_2$CH$_3$), 129.8 (aromat. C-2), 138.6 (aromat. C-1).

Synthesis of 1,3-Bis(thio-β-D-galactopyranosyldisulfanylmethyl)-5-methanethiosulfonatomethyl-2,4,6-trimethyl-benzene (44)

A solution of the methanethiosulfonate 40 (0.238 g, 0.48 mmol) in DMF (20 ml) was cooled under N$_2$ to 0° C. and the sodium salt of 1-thio-β-D-galactose (0.209 g, 0.96 mmol) in water (10 ml) was added over a period of 2 h using a syringe pump. After warming to room temperature over night, the solvents were removed under reduced pressure, and the resulting yellow oil was purified by flash chromatography (SiO$_2$, CHCl$_3$:MeOH :AcOH:H$_2$O, 60:30:3:5) to afford three products: 1,3-Bis(methane-thiosulfonatomethyl)-5-thio-β-D-galactopyranosyldisulfanylmethyl-2,4,6-trimethyl-benzene (0.048 g, 16%) as a colorless syrup, 44 (0.080 g, 23%) as a pale yellow solid, and tris-(thio-β-D-galactopyranosyldisulfanylmethyl)-mesitylene (0.210 g, 52%) as a white solid; analytical data of mono-Gal: $^1$H NMR (250 MHz, CD$_3$OD) δ 2.52 (s, 3H, CH$_3$), 2.56 (s, 6H, CH$_3$), 3.48 (s, 6H, SO$_2$CH$_3$), 3.59 (dd, 1H, J 9.5 and 3.3 Hz, H-3'), 3.65 (t, 1H, J 6.2 Hz, H-5'), 3.79 (dd, 1H, J 11.3 and 5.2 Hz, H-6a'), 3.86 (dd, 1H, J 11.2 and 6.7 Hz, H-6b'), 3.96–4.00 (m, 2H, H-2'/4 '), 4.29 (d, 1H, J 11.6 Hz, CHSS-Gal), 4.37 (d, 1H, J 11.6 Hz, CHSS-Gal), 4.44 (d, 1H, J 9.3 Hz, H-1'), 4.59 (s, 4H, CH$_2$SSO$_2$); $^{13}$C NMR (63 MHz, CD$_3$OD) δ 17.4 (CH$_3$), 17.8 (CH$_3$), 38.3 (CH$_2$SSO$_2$), 43.2 (CH2SS-Gal), 51.2 (SO$_2$CH$_3$), 63.8 (CH$_2$OH), 70.8, 71.3, 77.0 (C-3'), 82.0 (C-5'), 93.8 (C-1'), 131.0, 134.9, 139.5, 140.5; analytical data of 44: $^1$H NMR (500 MHz, CD$_3$OD) δ 2.53 (s, 6H, CH$_3$), 2.59 (s, 3H, CH$_3$), 3.35 (s, 3H, SO$_2$CH$_3$), 3.56 (dd, 2H, J 9.3 and 3.3 Hz, 2×H-3'), 3.62 (t, 2H, J 6.1 Hz, 2×H-5'), 3.77 (dd, 2H, J 11.3 and 5.6 Hz, 2×H-6a'), 3.82 (dd, 2H, J 11.4 and 6.5 Hz, 2×H-6b'), 3.93–3.97 (m, 4H, 2×H-2'/4'), 4.27 (d, 2H, J 11.4 Hz, 2×CHSS-Gal), 4.35 (d, 2H, J. 11.5 Hz, 2×CHSS-Gal), 4.40 (d, 2H, J 9.4 Hz, 2×H-1'), 4.58 (s, 2H, CH$_2$SSO$_2$); $^{13}$C NMR (125 MHz, CD$_3$OD) δ 16.7 (CH$_3$), 17.3 (CH$_3$), 37.5 (CH$_2$SSO$_2$), 42.4 (CH$_2$SS-Gal), 50.2 (SO$_2$CH$_3$), 62.8 (CH$_2$OH), 69.8, 70.5, 76.2 (C-3'), 81.1

(C-5'), 92.9 (C-1'), 129.4, 133.4, 138.6, 139.7; HRMS m/z (TOF ES+) Found 747.0736 (M+Na$^+$), $C_{25}H_{40}O_{12}S_6$ requires 747.0742; analytical data of tris-Gal: $^1$H NMR (300 MHz, D$_2$O) δ 2.65 (s, 3H, CH$_3$), 3.51–3.69 (m, 5H), 3.85–3.86 (m, 1H), –(m, 2H, CH$_2$OH), 4.24 (d, 1H, J 9.4 Hz, 2×H-1').

Attempted synthesis of 1,3-Bis (methanethiosulfonatomethyl)-5-thioacetylmethyl-2, 4,6-trimethyl-benzene (47 or 48)

The bromide 43 (0.611 g, 1.5 mmol) was dissolved in dry DMF (30 ml) under argon. Sodium methanethiosulfonate (0.403 g, 3 mmol) in dry DMF (5 ml) and potassium thioacetate (0.175 g, 1.5 mmol) in dry DMF (5 ml) were added simultaneously as fast as possible. After stirring for 35 h at room temperature, the solvent was removed under reduced pressure and the residue mixed with CH$_2$Cl$_2$ (30 ml) and water (50 ml). The phases were separated and the aqueous phase was extracted with CH$_2$Cl$_2$ (5×30 ml). The combined organic extracts were washed with brine, dried over MgSO$_4$, and evaporated. The residue was chromatographed (SiO$_2$, hexane: EtOAc, gradient elution, 1:1 to 0:1) to afford the following products: the thioacetate 45 (0.102 g, 18%) as an off-white solid, the methanethiosulfonate 46 (0.322 g, 44%) as an off-white solid, and 1,3-bis (thioacetylmethyl)-5-methanethiosulfonatomethyl-2,4,6-trimethyl-benzene (47; 0.096 g, 15%) as a colorless gum. A fourth isolated compound (white viscous foam, 0.088 g) is believed to be 48; analytical data of 45: $^1$H NMR (300 MHz, CDCl$_3$) δ 2.29 (s, 3H, CH$_3$), 2.36 (s, 6H, COCH$_3$), 2.39 (s, 6H, CH$_3$), 3.36 (s, 3H, SO$_2$CH$_3$), 4.20 (s, 4H, CH$_2$SAc), 4.48 (s, 2H, CH$_2$S); $^{13}$C NMR (75 MHz, CDCl$_3$) δ 16.3 (CH$_3$), 16.4 (CH$_3$), 29.6 (CH$_2$SAc), 30.4 (CH$_3$CO), 36.7 (CH$_2$SSO$_2$), 50.1 (SO$_2$ CH$_3$), 127.8 (aromat. C-4/6), 131.8 (aromat. C-1/3), 136.6 (aromat. C-2), 137.5 (aromat. C-5), 195.7 (C=O). Both spectra contain additional signals due to impurities.

Synthesis of 1,3,5-Tris(methoxycarbonyl)benzene
(S. M. Dimick, S. C. Powell, S. A. McMahon, D. N. Moothoo, J. H. Naismith. E. J. Toone, *J. Am. Chem. Soc.* 1999. 121 10286–10296)

In a flask equipped with a condenser and a drying tube 1,3,5-benzenetricarboxylic acid 49 (22.12 g, 0.1 mol) was suspended in methanol (250 ml), concentrated sulphuric acid (25 ml) was added, and the mixture was refluxed over night. After cooling to 0° C. the white precipitate was filtered off, washed with cold water, dissolved in CHCl$_3$, and dried over MgSO$_4$. Removal of the solvent gave the desired product (22.05 g, 87%) as a white powder; mp 142–144° C. (lit. 144–144.5° C.); $^1$H NMR (300 MHz, CDCl$_3$) δ 3.99 (s, 3H, CH$_3$), 8.85 (s, 1H, aromat. H).

Synthesis of 1,3,5-Tris(hydroxymethyl)benzene (50)
(Y. Yamaqiwa, Y. Koreishi. S. Kivozumi, M. Kobavashi, T. Kamikawa, M. Tsukino, H. Goi, M.

Yamamaoto, M. Munakata. Bull. Chem. Soc. Jpn. 1996, 69, 3317–3323; J. Houk, G. Whitesides. J. Am. Chem. Soc. 1987, 109, 6825–6836)

A solution of 1,3,5-tris(methoxycarbonyl)benzene (10.09 g, 40 mmol) in dry THF (400 ml) was added over a period of 3h to a suspension of LiAlH$_4$ (4.03 g, 0.1 mol) in dry THF (300 ml) under N$_2$. After stirring over night at room temperature, the reaction mixture was cooled to 0° C., hydrolysed with water (4 ml), 2M NaOH (4 ml) and water (12 ml), filtered, and the filter cake washed thoroughly with THF. The combined filtrates were concentrated and the crude product was recrystallized from hot (not boiling) ethanol to afford 50 (5.59 g, 83%) as white needles; mp 76–77° C. (lit. 77–78° C.) $^1$H NMR (300 MHz, DMSO-d6) δ 4.49 (d, 3H, J 4.8 Hz, CH$_2$), 5.30 (t, 1H, J 5.4 Hz, OH), 7.14 (s, 1H, aromat. H).

5 Modification of SBL-S156C with 44

In a polypropylene test-tube 16.1 mg of S156C was dissolved in 2.4 ml modification buffer (70 mM CHES, 5 mM MES, 2 mM CaCl$_2$, pH 9.5), mixed with 100 μl of a 0.25 M solution of 21 in water/CH$_3$CN (2/1), vortexed, and allowed to react using an end-over-end rotator at room temperature. After 30 min 10 μl of the reaction mixture were withdrawn and tested for residual free thiol content by mixing with 10 μl Ellman's reagent (2.5*10$^{-2}$ M in pH 6.9 phosphate buffer). The absence of yellow color by visual inspection indicated complete reaction. An additional 100 μl of the 0.25 M solution of 21 was added and the mixture permitted to react for a further 30 min. The reaction then was quenched by pouring the reaction mixture onto a pre-packed, pre-equilibrated G-25 Sephadex PD10 column and eluted with 3.5 ml of quench buffer (5 mM MES, 2 mM CaCl$_2$, pH 6.5). The eluant was dialyzed at 4° C. against 10 mM MES, 2 mM CaCl$_2$, pH 5.8 (3×21, 3×60 min). The resulting dialysate was aliquoted, flash frozen in liquid nitrogen, and stored at –18° C.

Example 4

Modification of Cysteine-Containing Protein with 2-(β-D-galactopyranosyl)ethyl Methanethiosulfonate A cysteine-containing mutant of subtilisin *Bacillus lentus*, S156C, was modified with the glycoMTS reagent 2-(β-D-galactopyranosyl)ethyl methanethiosulfonate to give the glycoprotein S156C-SS-ethyl 2-(β-D-galactopyranose) following procedures outlined in Example 3. This resulted in a CMM enzyme ("gal-protease") illustrated in FIG. 18.

Experimental

Preparation of 2-(β-D-Galactopyranosyl)ethyl Methanethiosulfonate

A solution of NaOMe (0.104 m, 0.8 ml) was added to a solution of 2-(2,3,4,6-TetraO-acetyl-β-D-galactopyranosyl) ethyl methanethiosulfonate 11 (778 mg, 1.71 mmol) in MeOH) (10 ml) under N$_2$. After 4 hours, the reaction solution was passed through a Dowex 50W(H$^+$) plug (3×1 cm, eluant MeOH), and the solvent removed to give 2-bromoethyl β-D-galactopyranoside (450 mg, 92%) as a white solid which was used directly in the next step. NaSSO$_2$CH$_3$ (180 mg, 1.34 mmol) was added to a solution of 2-bromoethyl β-D-galactopyranoside (290 mg, 1.01 mmol) in DMF (12 ml) under N$_2$ and warmed to 50° C. after 15 hours, the solution was cooled and the solvent removed. The residue was purified by flash chromatography (MeOH: ETOAc, 1:9 to give the title compound (229 mg., 71% as a white foam). Characterization of the compound so produced is found in application serial number 09/347,029 "Chemically Modified Proteins with a Carbohydrate Moiety."

Example 5

Catalytic Activity of Modified Enzymes

Lectin-mediated interactions between oral viridans group streptococci and actinomyces may play an important role in microbial colonization of the tooth surface. Oral actinomycetes and streptococci freshly isolated from dental plaque are known to coaggregate via lactose-reversible cell—cell interactions. This finding suggests that the coaggregation is mediated by a network of lectin-carbohydrate interactions between complementary cell surface structures on the two cell types. Kolenbrander P E, Williams B L., "Lactose-reversible coaggregation between oral actinomycetes and Streptococcus sanguis" *Infect Immun.* 1981 July;33(1):95–102.

The presence of two host-like motifs, either GalNAc beta—>3Gal (Gn) or Gal betal—>GalNAc (G), in the cell wall polysaccharides of five streptococcal strains, including *S. sanguis*, accounts for the lactose-sensitive coaggregations of these bacteria with *Actinomyces naeslundui*. Cisar J O, Sandberg A L, Reddy G P. Abeygunawardana C, Bush C A, "Structural and antigenic types of cell wall polysaccharides from viridans group streptococci with receptors for oral actinomyces and streptococcal lectins," *Infect Immun.* 1997 December;65(12):5035–41. The *S. sanguis* receptor for the actinomyces lectin comprises repeating hexasaccharide units with Galactose, N-acetylgalactosamine (GalNAc) termini. The agglutination of oral streptococci strains by the actinomyces lectin activity blocks attachment of actinomyces to epithelial cells, and this is thought to inhibit the killing of actinomyces by polymorphonuclear leukocytes. Mergenbagen S E, Sandberg A L, Chassy B M, Brennan M J, Yeung M K, Donkersloot J A, Cisar J O, "Molecular basis of bacterial adhesion in the oral cavity," *Rev Infect Dis.* 1987 September–October;9 Suppl 5:S467–74.

The ability of two different glycodendrimer proteins to inhibit the lectin activity of the bacteria *A. naeslundii* was tested to determine whether the attachment of one or two galactose moieties to the enzyme would modify the substrate specificity of the enzyme so that it can recognize and digest the lectin.

A coaggregation experiment was carried out according to methods similar to those described in Kolenbrander P E, Williams B L., "Lactose-reversible coaggregation between oral actinomycetes and Streptococcussanguis," *Infect Immun.* 1981 July;33(l):95–102. *A. naeslundii* was pretreated with subtilisin *Bacillus lentus* protease or S156C-SS-ethyl 2-(β-D-galactopyranose) ("gal-protease") (enzyme concentration 50 ug/ml) in the presence or absence of lactose (60–300 ug/ml), and the ability of the treated *A. naeslunddi* to co-aggregate w/*S. sanguis* was determined by microscopic evaluation. The amount of coaggregation (i.e., lectin activity), from highest to lowest is listed in Table 1, below.

TABLE 1

CoAggregation of *A. naeslundii* and *S. sanguis* untreated *A. naeslundii* ≈ *A. naeslundii* treated with protease(50 ug/ml) - *A. naeslundii* treated with gal-protease(50 ug/ml)
*A. naeslundii* treated with protease(lactose in the enzyme reaction mix)
*A. naeslundii* treated with gal-protease(lactose in the enzyme reaction mix)

In a second experiment, the ability of the protease, the gal-protease and the di-gal protease to block attachment of *A. naestundii* to human buccal epithelial cells was tested. The epithelial cells were treated with *C. perfringens* neuraminidase to remove terminal sialic acid residues (thus exposing galactose). *A. naeslundii* were incubated with one of the three proteases at a protease concentration of 10 ug/ml in the presence or absence of lactose. Attachment was assayed by labeling the bacteria with a fluorescein tag that is internalized by the bacteria (thereby not disturbing the bacteria's adhesive structures (i.e., the surface fimbrae). Following incubation of the buccal cells with the fluorescein-labeled bacteria, the number of bacteria adhering to the buccal cells was analyzed by running the reaction mix through a flow cytometer. The counts shown below in Table 2, are average counts per buccal cell, and so roughly correspond to the number of bacteria attaching to each cell.

TABLE 2

Buccal Cell Adhesion Assay Results

| Enzyme | Lactose | Counts |
| --- | --- | --- |
| gal-protease | − | 302 |
| gal-protease | + | 313 |
| di-gal-protease | − | 118 |
| di-gal protease | + | 237 |
| protease | − | 190 |
| protease | + | 321 |
| — | − | 470 |
| — | + | 813 |

The results of this assay demonstrate that di-gal protease produces a greater reduction in the number of *A. naeslundii* adhering to the buccal epithelial cells, as compared to untreated bacteria and those treated with the control S156C protease. Interestingly, and in contrast to the coaggregation assay results, the presence of lactose appears to potentiate the binding of *A. naeslundii* to human buccal epithelial cells under the conditions of this assay.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for producing a glycodendrimer, comprising the steps of:
   a) providing a first dendrimer core building block, an alkylthiosulfonate, and a carbohydrate having a first sulfhydryl group;
   b) reacting said first dendrimer core building block with said alkylthiosulfonate to produce a modified dendrimer core building block having an alkylthiosulfonate group;
   c) reacting said modified dendrimer core building block with said carbohydrate to produce a glycodendrimer.

2. The method of claim 1, wherein said alkylthiosulfonate is methanethiosulfonate.

3. The method of claim 2, wherein said methanethiosulfonate is a salt.

4. The method of claim 1, wherein said first dendrimer core building block is tris(2-aminoethyl)amine.

5. The method of claim 1, wherein said first dendrimer core building block is pentaerythritol.

6. The method of claim 1, wherein said first dendrimer core building block is mesitylene or mesitylene tribromide.

7. The method of claim 1, wherein said carbohydrate is directly linked to said first sulfhydryl group.

8. The method of claim 1, wherein said carbohydrate is tethered to said first sulfhydryl group.

9. The method of claim 1, wherein said carbohydrate comprises a monosaccharide.

10. The method of claim 9, wherein said monosaccharide is selected from the group consisting of galactose, glucose and mannose.

11. The method of claim 1, wherein said glycodendrimer produced in step c) is a first-generation glycodendrimer.

12. The method of claim 11, wherein said first-generation glycodendrimer comprises an alkylthiosulfonate group.

13. The method of claim 12, wherein said alkylthiosulfonate group is methanethiosulfonate.

14. The method of claim 1, further comprising the steps of:
   d) reacting said modified dendrimer core building block having an alkylthiosulfonate group with a second dendrimer core building block having a second sulfhydryl group to produce a multi-generation glycodendrimer.

15. The method of claim 14, wherein said multi-generation glycodendrimer is a second-generation glycodendrimer.

16. The method of claim 14, wherein said carbohydrate is directly linked to said first sulfhydryl group.

17. The method of claim 14, wherein said second carbohydrate is tethered to said first sulfhydryl group.

18. The method of claim 14, wherein said carbohydrate comprises a monosaccharide.

19. The method of claim 14, wherein said monosaccharide is selected from the group consisting of galactose, glucose and mannose.

20. The method of claim 19, wherein said monosaccharide is galactose.

21. The method of claim 19, wherein said monosaccharide is glucose.

22. A method for producing a glycodendrimer, comprising the steps of:
   a) providing a dendrimer core having a carbohydrate group, a first sulfhydryl group, and a second sulfhydryl group, and an alkylthiosulfonate having at least two thiosulfonate groups, and
   b) reacting said dendrimer core with said alkylthiosulfonate to produce a multi-generation glycodendrimer.

23. The method of claim 22, wherein said at least two thiosulfonate groups comprise a methanethiosulfonate.

24. The method of claim 22, wherein said alkylthiosulfonate is a bis-methanethiosulfonate.

25. The method of claim 24, wherein said bis-methanethiosulfonate is synthesized from tris(2-aminoethyl)amine.

26. The method of claim 22, wherein said alkylthiosulfonate is a tris-methanethiosulfonate group.

27. The method of claim 26, wherein said tris-methanethiosulfonate group is tris(methanethiosulfonatemethyl)mesitylene.

28. The method of claim 22, wherein said carbohydrate group is directly linked to said first sulfhydryl group.

29. The method of claim 22, wherein said carbohydrate is tethered to said first sulfhydryl group.

30. The method of claim 22, wherein carbohydrate comprises a monosaccharide.

31. The method of claim 30, wherein said monosaccharide is selected from the group consisting of galactose, glucose and mannose.

32. The method of claim 31, wherein said monosaccharide is galactose.

33. The method of claim 31, wherein said monosaccharide is glucose.

34. The method of claim 31, wherein said monosaccharide is mannose.

35. The method of claim 31, wherein said dendrizner core is synthesized from tris(2-aminoethyl)amine.

36. The method of claim 22, wherein said dendrimer core is synthesized from pentaerythritol.

37. The method of claim 22, wherein said dendrimer core is synthesized from mesitylene tribromide.

38. The method of claim 22, wherein said multi-generation glycodendrimer is a second-generation glycodendrimer.

* * * * *